(12) United States Patent
Rucker et al.

(10) Patent No.: US 10,178,955 B2
(45) Date of Patent: Jan. 15, 2019

(54) ENHANCED METHOD FOR CORRECTING DATA FOR DEFORMATIONS DURING IMAGE GUIDED PROCEDURES

(71) Applicants: Daniel Caleb Rucker, Nashville, TN (US); Michael I. Miga, Franklin, TN (US)

(72) Inventors: Daniel Caleb Rucker, Nashville, TN (US); Michael I. Miga, Franklin, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 123 days.

(21) Appl. No.: 13/960,326

(22) Filed: Aug. 6, 2013

(65) Prior Publication Data

US 2014/0037161 A1  Feb. 6, 2014

Related U.S. Application Data

(60) Provisional application No. 61/679,830, filed on Aug. 6, 2012.

(51) Int. Cl.
*G06T 7/33* (2017.01)
*A61B 5/00* (2006.01)
(Continued)

(52) U.S. Cl.
CPC ............ *A61B 5/0033* (2013.01); *A61B 34/20* (2016.02); *G06T 7/30* (2017.01); *G06T 7/344* (2017.01)

(58) Field of Classification Search
CPC ....... G06T 7/0028; G06T 2207/300004; G06T 2207/10072; G06T 7/0012;
(Continued)

(56) References Cited

U.S. PATENT DOCUMENTS 6,369,815 B1 * 4/2002 Celniker ................. G06T 17/00
  345/420
6,718,291 B1 * 4/2004 Shapiro ............... G06F 17/5018
  703/14
(Continued)

FOREIGN PATENT DOCUMENTS

CN  102034725 A  4/2011
WO  2011091218 A1  7/2011

OTHER PUBLICATIONS

Declerck et al., Automatic Retrieval of Anatomical Structures in 3D Medical Images, 1995 [retrieved Jun. 6, 2017], Computer Vision, Virtual Reality and Robotics in Medicine: Lecture Notes in Computer Science, vol. 905,pp. 153-162. Retrieved from the Internet: https://link.springer.com/chapter/10.1007/978-3-540-49197-2_17.*
(Continued)

*Primary Examiner* — Andrew Moyer
*Assistant Examiner* — Dennis Rosario
(74) *Attorney, Agent, or Firm* — Nixon Peabody LLP; Eduardo J. Quiñones

(57) ABSTRACT

Systems and methods are provided for collecting and processing physical space data for use while performing an image-guided surgical (IGS) procedure. A method includes performing a rigid alignment of a computer model of a non-rigid structure of interest in a patient and surface data in a patient space associated with at least a portion of said non-rigid structure, and computing a deformation of the computer model that provides a non-rigid alignment of said computer model and an organ geometric representation of data, said deformation computed using a set of boundary conditions and field variables defined for said computer model based on said rigid alignment and a parameterization function.

12 Claims, 18 Drawing Sheets

(51) Int. Cl.
 *A61B 34/20* (2016.01)
 *G06T 7/30* (2017.01)
(58) Field of Classification Search
 CPC ......... G06T 2207/10081; G06T 7/0024; G06T 2207/10088; G06T 2210/41; G06T 2207/30004; G06T 7/30; G06T 7/344; G06F 7/5018; A61B 6/032; A61B 34/10; A61B 34/20; A61B 2034/105; G06K 9/00147
 See application file for complete search history.

(56) References Cited

U.S. PATENT DOCUMENTS

| | | | | |
|---|---|---|---|---|
| 7,257,244 B2* | 8/2007 | Miga | ...................... | G06T 7/0012 382/128 |
| 7,363,180 B2* | 4/2008 | Swaringen | .............. | B23K 26/04 702/85 |
| 7,676,255 B2* | 3/2010 | Wang | ....................... | A61B 6/04 5/600 |
| 7,828,735 B2* | 11/2010 | Holmes | ................... | A61B 5/055 600/450 |
| 8,233,681 B2* | 7/2012 | Aylward | ................ | A61B 19/52 382/128 |
| 2008/0123927 A1* | 5/2008 | Miga | ...................... | A61B 19/52 382/131 |
| 2008/0221425 A1* | 9/2008 | Olson | .................... | A61B 90/36 600/407 |
| 2014/0044333 A1* | 2/2014 | Barth, Jr. | .............. | G06T 7/0028 382/131 |

OTHER PUBLICATIONS

Bookstein, Principal Warps: Thin-Plate Splines and the Decomposition of Deformations, Jun. 1989 [retrieved Jun. 5, 2017], IEEE Transactions on Pattern Analysis and Machine Intelligence, vol. 11, Issue: 6, pp. 567-585. Retrieved from the Internet: http://ieeexplore.ieee.org/document/24792/#full-text-section.*
Chinese Office Action dated Jun. 1, 2016 for corresponding Chinese Patent Application No. 201380042086.8.
American Cancer Society, "Cancer Facts and Figures", American Cancer Society (2004) Atlanta.
Antipolis, "Project-team epidaure: Epidaure, project images, diagnostic, automatique, robotique medical imaging, & robotics", INRIA 2003. (50 pages).
Ayache, "Epidaure: A research project in medical image analysis, simulation, and robotics at INRIA", IEEE Trans Med Imaging (2003) 22: 1185-1201.
Bao et al., "Ultrasound-to-computer-tomography registration for image-guided laparoscopic liver surgery", Surg. Endosc. (2005).
Barnes et al., "A novel model-gel-tissue assay analysis for comparing tumor elastic properties to collagen content", Biomech Model Mechanobiol (2009).
Barnes et al., "Development of a mechanical testing assay for fibrotic murine liver", Medical Physics (2007) 34 (11): 4439-4450.
Barnes, et al., "Development of a mechanical testing assay for modulus analysis of fibrotic murine livers", 6th International Conference on the Ultrasonic Measurement and Imaging of Tissue Elasticity, Santa Fe, New Mexico, (Nov. 2007): 48.
Blackall et al., "A statistical model of respiratory motion and deformation of the liver", Medical Image Computing and Computer-Assisted Interventions, S. Verlag, Ed. Berlin (2001) 2208: 1338-1340.
Blumgart et al., "Surgical options in the treatment of hepatic metastases from colorectal cancer", Curr. Prob. Surg. (1995) 35: 336-413.
Bradley et al., "Surgical experience with hepatic colorectal metastasis", Am. Surg. (1999) 65: 560-567.

Cash et al., "Compensating for intraoperative soft-tissue deformations using incomplete surface data and finite elements", IEEE Transactions on Medical Imaging (2005) 24: 1479-1491.
Cash et al., "Concepts and preliminary data toward the realization of image-guided liver surgery", Gastrointest Surg (2007) 11: 844-859.
Clements et al., "Atlas-based method for model updating in image-guided liver surgery", SPIE Medical Imaging 2007: Visualization, Image Guided Procedures, and Modeling, San Diego, CA. (12 pages).
Clements et al., "Organ surface deformation measurement and analysis in open hepatic surgery: Method and preliminary results from 12 clinical cases", IEEE Transactions on Biomedical Engineering (2011) 58(8): 2280-2289.
Clements et al., "Robust surface registration using salient anatomical features for image-guided liver surgery: Algorithm and validation", Medical Physics (2008) 35(6): 2528-2540.
Clements et al., "Salient anatomical features for robust surfaces registration and atlas-based model updating image-guided liver surgery," Ph.D. Dissertation, Vanderbilt University, Department of Biomedical Engineering (2009). (171 pages).
Cohnert et al., "Preoperative risk assessment of hepatic resection for malignant disease", World J. Surg. (1997) 21: 396-400.
Dematteo et al., "Anatomic segmental hepatic resection is superior to wedge resection as an oncologic operation for colorectal liver metastases", J. Gastrointest. Surg. (2000) 4: 178-184.
Dumpuri et al., "Comparison of pre/post-operative CT image volumes to preoperative digitization of partial hepatectomies: A feasibility study in surgical validation", SPIE Medical Imaging 2009: Visualization, Image-Guided Procedures and Modeling Conference. (7 pages).
Dumpuri et al., "Model-updated image-guided liver surgery: preliminary results using intraoperative surface characterization", SPIE 2010: Medical Imaging Visualization, Image-Guided Procedures, and Modeling Conference. (7 pages).
Fericks et al., "3D CT modeling of hepatic vessel architecture and volume calculation in living donated liver transplantation", Eur J Radiol (2004) 14: 326-333.
Hackworth et al., "A dual compute resource strategy for computational model assisted therapeutic interventions", SPIE Medical Imaging 2009: Visualization, Image-Guided Procedures, and Modeling (2009) 7261: 72612R1-7.
Hartkens et al., "Measurement and analysis of brain deformation during neurosurgery", IEEE Transactions on Medical Imaging (2003) 22: 82-92.
Hermoye et al., "Liver segmentation in living liver transplant donors: Comparison of semiautomatic and manual methods", Radiology (2005) 234: 171-178.
Jarnagin et al., "Improvement in perioperative outcome after hepatic resection: analysis of 1803 consecutive cases over the past decade", Ann. Surg. (2002) 236: 397-406.
Knaus et al., "System for laparoscopic tissue tracking", IEEE Symposium on Biomedical imaging, Washington, D.C. (2006). (4 pages).
Lang et al., "Extended left hepatectomy—modified operation planning based on three-dimensional visualization and liver anatomy", Langenbecks Arch Surg. (2004) 389: 306-310.
Laurent et al., "Influence of postoperative morbidity on long-term survival following liver resection for colorectal metastases", Br. J. Surg., (2003) 90: 1131-1136.
Lorenson et al., "Marching cubes: A high resolution 3d surface construction algorithm", ACM Computer Graphics, (1987) 21: 163-169.
Matasuni et al., "Modally controlled free form deformation for non-rigid registration in image-guided liver surgery", Medical Image Computing and Computer-Assisted Interventions, S. Verlag, Ed. Berlin (2001) 2208: 1275-1278.
Maurer et al., "Registration of 3D images using weighted geometrical features", IEEE Transactions on Medical Imaging (1996) 15(6): 836-849.

(56) References Cited

OTHER PUBLICATIONS

Miga et al., "Intraoperative registration of the liver for image-guided surgery using laser range scanning and deformable models", Medical Imaging 2003: Visualization, Image-guided Procedures, and Display (2003): 350-359.

Miga, "The changing roles for soft-tissue modeling: Therapy guidance", Workshop on Clinical Image-Guided Therapy: Opportunities and Needs, Sponsored by the National Institutes of Health and National Center for Image-Guided Therapy, Washington D.C. (Mar. 2008). (1 page).

Nabavi et al., "Image-guided therapy and intraoperative MRI in neurosurgery", Minimally Invasive Therapy & Allied Technologies (2000) 9: 277-286.

Nabavi et al., "Serial intraoperative magnetic resonance imaging of brain shift", Neurosurgery (2001) 48: 787-797.

Nimsky et al., "Intraoperative magnetic resonance tomography—experiences in neurosurgery", Nervenarzt (2000) 71: 987-994.

Nimsky et al., "Quantification of, visualization of, and compensation for brain shift using intraoperative magnetic resonance imaging", Neurosurgery (2000) 47:1070-1078.

Penney et al., "Registration of freehand 3D ultrasound and magnetic resonance liver images", Medical Image Analysis (2004) 8: 81-91.

Scheele et al., "Resection of colorectal liver metastasis", World J. Surg., (1995) 19: 59-71.

Schindl et al., "The value of residual liver volume as a predictor of hepatic dysfunction and infection after major liver resection", Gut (2005) 54: 289-296.

Selle et al., "Analysis of vasculature of liver surgical planning", IEEE Trans Med Imaging (2002) 21:1344-1257.

Sheiner et al., "Treatment of metastatic cancer to the liver", Seminars in Liver Disease (1994) 14(2):169-177.

Stevanovic et al., "Modeling contact between rigid sphere and elastic layer bonded to rigid substrate", IEEE Trans on Components and Package Technologies (2001) 24: 207-212.

Stone et al., "Surgical therapy for recurrent liver metastases from colorectal cancer", Arch Surg. (1990) 125: 718-722.

Sunthau et al., "A concept work for augmented reality visualization based on a medical application in liver surgery", Proc. of the ISPRS Commission V Symposium, Corfu, Greece, (2002): 274-280.

Yamamoto et al., "Pathologic support for limited hepatectomy in the treatment of liver metastases from colorectal cancer", Ann. Surg. (1995) 221: 74-78.

* cited by examiner

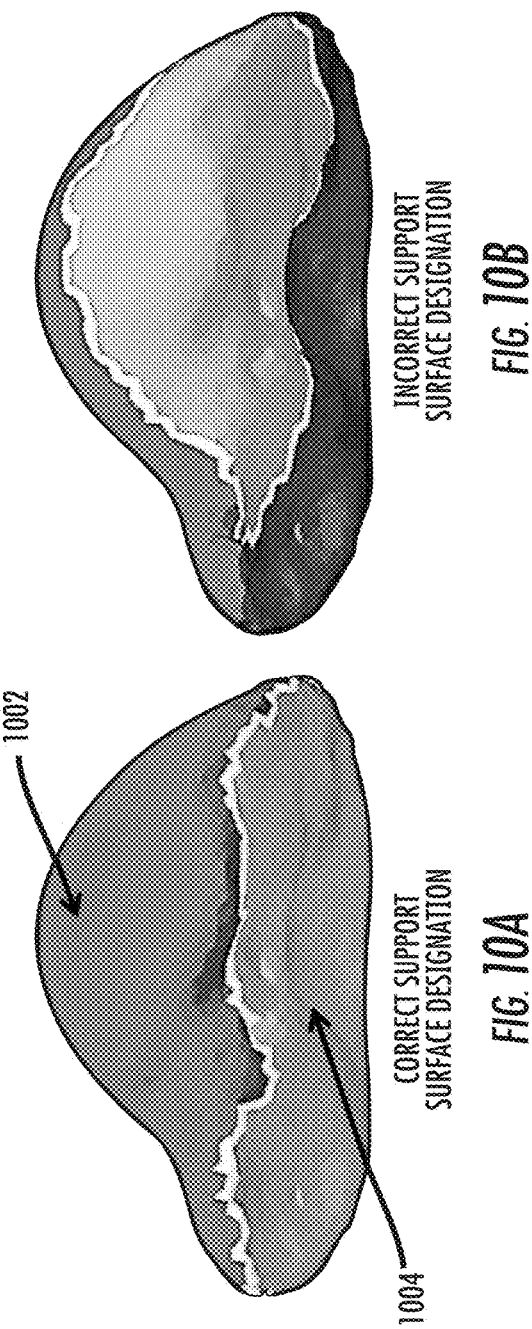

ENHANCED METHOD FOR CORRECTING DATA FOR DEFORMATIONS DURING IMAGE GUIDED PROCEDURES

CROSS REFERENCE TO RELATED APPLICATIONS

This application claims the benefit of U.S. Provisional Application Ser. No. 61/679,830 entitled "ENHANCED METHOD FOR CORRECTING DATA FOR DEFORMATIONS DURING IMAGE GUIDED PROCEDURES", filed Aug. 6, 2012, the contents of which are herein incorporated by reference in their entirety.

STATEMENT REGARDING FEDERALLY FUNDED RESEARCH

This invention was made with government support under NIH No. 1R01CA162477-01 awarded by National Institutes of Health (National Cancer Institute). The government has certain rights in the invention.

FIELD OF THE INVENTION

The present invention relates to systems and methods for image-guided procedures, and more specifically to systems and methods for correcting tissue data for deformations during image guided procedures.

BACKGROUND

Briefly, a process of nonrigidly fitting an organ computer model built from imaging data to the intraoperative environment and providing a novel transform to represent that within an image-guided surgery systems is the context of WO2011/091218 A1 to Miga et al., published Jul. 28, 2011, and entitled "SYSTEM AND METHOD FOR CORRECTING DATA FOR DEFORMATIONS DURING IMAGE-GUIDED PROCEDURES" (hereinafter "Miga"), the contents of which are herein incorporated by reference in their entirety. Briefly, Miga describes a process that begins subsequent to an initial rigid alignment between intraoperatively acquired organ geometry data and an organ geometry representation of the preoperative organ state. In this realization, the organ surface is captured intraoperatively by a laser range scanner of the anterior surface primarily, and the organ geometry is extracted from CT scans to generate a 3 dimensional computer model. Miga also describes a suite of techniques that looks at the discrepancy between the alignment of the anterior intraoperative surface and the corresponding computer model anterior surface after rigid alignment. Once this discrepancy is assessed, usually by a signed closest point distance, the information is used to extrapolate a distribution of boundary conditions outside the correspondence area for the process of correcting deformation. Once the full volumetric field of deformation is generated, the stylus alignment transform takes over and corrects the surgical guidance platform for nonrigid effects.

SUMMARY

The various embodiments of the invention improve accuracy over the methods of Miga and others by developing a new nonrigid registration approach which reconstructs the likely physical causes of deformation, and to improve efficiency by not requiring a finite element tissue model to be solved in the intraoperative setting. The approach of the various embodiments aligns a biomechanical liver model (built from preoperative images) to incomplete geometric data that represents sparse liver region locations gathered intraoperatively (e.g. anterior surfaces, tumor centroids). Unlike prior methods that were extrapolative in nature, the approach of the various embodiments casts the nonrigid registration as a nonlinear optimization problem. Based on very limited surgical organ presentation assumptions, a set of boundary conditions is parameterized on the deformation-inducing regions of the organ surface. Those parameters are then reconstructed via an iterative algorithm which minimizes the error between the incomplete geometric data and the deformed model counterpart, where precise correspondence is not known or assumed a priori.

In a first embodiment of the invention, there is provided a method for collecting and processing physical space data for use while performing an image-guided surgical (IGS) procedure. The method includes performing a rigid alignment of a computer model of a non-rigid structure of interest in a patient and surface data in a patient space associated with at least a portion of said non-rigid structure, and computing a deformation of the computer model that provides a non-rigid alignment of said computer model and an organ geometric representation of data, said deformation computed using a set of boundary conditions and field variables defined for said computer model based on said rigid alignment and a parameterization function.

In this method, a functional form of the parameterization function can be at least one among a continuous functional form, an overlapping functional form, or multi-domain coupled functional form. Further, the computing can include performing an iterative fitting process comprising varying at least one of a kernel or a parameter of a functional form of the parameterization function. The iterative fitting process can be based on the contributing deformations from at least one of the kernel or parameters being varied.

In a second embodiment of the invention, there is provided another method for collecting and processing physical space data for use while performing an image-guided surgical (IGS) procedure. This method includes establishing a correspondence relationship between an organ geometric representation of data-points acquired intraoperatively of the non-rigid structure of interest in a patient and points on an organ geometric representation computer model for the non-rigid structure of interest such that corresponding points are determined. The method also includes computing a closeness of fit metric for the entire dataset based on three-dimensional (3D) vectors which connect the corresponding points and other geometric features of the non-rigid structure, and determining a set of deformation modes for a subset of the organ geometric representation computer model, where the set of deformation modes are computed via the solution of the organ geometric representation computer model, where the boundary conditions and/or field variables are determined by a set of parameter values, and where the deformation nodes are associated with any portion of the organ geometric representation computer model. The method additionally includes using a nonlinear optimization framework, iteratively choosing a set of parameter values to minimize the closeness metric, where the set of parameter values define a deformation of the subset of the organ geometric representation computer model, and where the choosing is based on any type of information regarding the organ geometric representation data-points or a surrounding environment that is associated with nonrigid structure. The method also includes, subsequent to the step of choosing, redetermining the correspondence relationship and applying boundary conditions on a remainder of the organ geometric representation computer model to eliminate any remaining organ fitting error.

In this method, the step of choosing can further include repeating, until a termination condition is met, an iteration consisting of: selecting an candidate set of parameters, computing a deformation of the subset of the organ geometric representation computer model based on the candidate set of parameters, adjusting the computer model to conform to the organ geometric representation data points by applying a deformation field to yield an adjusted computer model, computing a correspondence between the organ geometric representation data and the organ geometric representation of the adjusted computer model, and evaluating the a correspondence (absolute or approximated) metric between the adjusted computer model and the organ geometric representation data-points. The termination condition can be based on the closeness of fit metric and the candidate set of parameters is selected to lower the closeness of fit metric during each iteration. Further, the candidate set of coefficients can be selected using a Levenberg-Marquardt, Newton, Quasi-Newton, Line-Search, Trust Region, Simplex-based, Genetic Algorithm, or similar optimization update procedure.

In the method, the portion of the organ geometric representation computer model can be at least one of and internal portion and an external portion. Further, the information regarding the organ geometric representation data-points or a surrounding environment that is associated with nonrigid structure can be behavior information.

In a third embodiment of the invention, there is provided a computer-readable storage medium, having stored thereon a plurality of instructions for causing a computing device to perform the methods of the first and second embodiments.

In a fourth embodiment of the invention, there is provided a system including a processor and a computer-readable storage medium, the computer-readable storage medium having stored thereon a plurality of instructions for causing the processor to perform the methods of the first and second embodiments.

BRIEF DESCRIPTION OF THE DRAWINGS

FIGS. 10A and 10B illustrate examples of correct and incorrect support surface designations;

DETAILED DESCRIPTION

Figure 1:
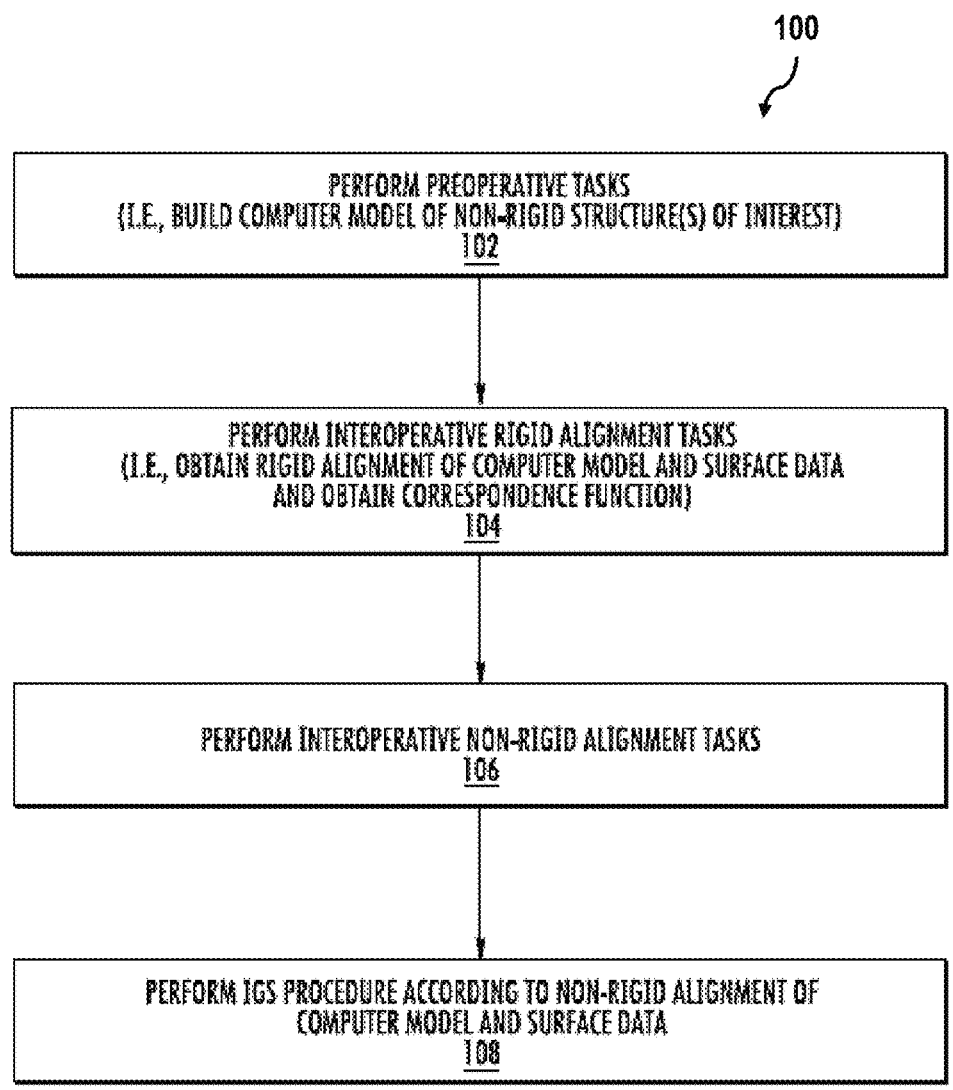
FIG. 1 is a flowchart showing steps in an exemplary method for performing an IGS procedure in accordance with an embodiment of the invention.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The invention that has been generated represents a complete solution to correct for the misregistration of data due to the presence of intraoperative deformation during image/data-guided surgery. The solution requires both standard and custom-built software components and can be controlled on standard compute/controller hardware. Interaction with image-guided image systems can be achieved through a variety of standard interfaces (serial, USB, Ethernet, Wireless, etc.).

This disclosure represents a nonrigid deformation compensation approach related to that described in Miga, yet the realization is completely different. This approach of the present disclosure begins by selecting a region of the computer model whose boundary conditions and other field quantities are to be parameterized with a functional form. In Miga, parameterization was limited to discrete domains whereas a functional form allows for a small subset of parameters/coefficients to define behavior in a larger region. The potential advantage is a reduction in the number of parameters sought.

In addition, the approach of the present disclosure also performs a strategy of pre-computing modes of deformation based on the parameterization. More specifically, the impact of deformation of an individual parameter perturbation can be pre-computed, so if active in the fitting process intraoperatively, it can be computed very quickly for increased speed of registration.

The other aspect of the present disclosure that is quite different than Miga is the region selected for parameterization need not be the approximated corresponding surface with the intraoperative data. In the examples provided below, the posterior side of the liver computer model is specifically parameterized when the intraoperative data is reflective of the anterior side. The fitting process will apply boundary conditions on the posterior surface to fit the anterior intraoperative surface data. This has the advantage over Miga of being similar to what is done intraoperatively in real operating rooms for open liver resection, i.e. often the liver is packed from underneath with deformations applied from underneath causing shape change on the anterior surface.

Additionally, with this approach, it allows for other information to drive the fitting process. For example, it is possible for internal structures to be known using various imaging methods. There is no reason that in conjunction with fitting an anterior surface, one could not also fit an internal structure as part of the process (e.g. a blood vessel or tumor) provided it can be sampled intraoperatively (perhaps by ultrasound). The approach claimed here also provides some latitude to prescribe things like collision conditions. For example, one may want a collision condition specified with the abdomen wall and modify the constraints of parameterization to reflect this.

Also, while iterative algorithms are mentioned in Miga, they are primarily concerned with the alternation between rigid and nonrigid algorithms. In this disclosure, an iterative nonlinear optimization algorithm cast as an objective function for fitting the anterior surface is done which allows for algorithmic approaches such as Levenberg-Marquardt to be used. This recasts the fitting process similar to common least-squares inverse problems, as opposed to the single-solve non-iterative fitting process of Miga.

Lastly, many of the registration, model generation steps, and biomechanical model type designations of Miga are compatible with the approaches of the present disclosure. In addition, the present disclosure represents another approach to generating the full volumetric deformation field which is completely compatible with the stylus transform of Miga for updating the guidance system.

The solution begins with a preoperative phase in which the preoperative images of the organ of interest from the patient are processed to generate a computer model as well as to derive any other possible data that could be necessary to perform deformation compensation within the operative environment (e.g. generate a distribution of deformation shapes to be used in a fitting process, or preoperative image analysis for enhanced feedback, computer mesh generation, pre-operative generation of mathematical functions to assist fitting, the designation/segmentation of organ shapes or partial surfaces (e.g. anterior surface of liver or tumor boundary etc.)). This preoperative phase can either be done on standard or enhanced computer architectures which may include the intraoperative correction computer controller itself or on separate more advanced computer hardware (GPU-based platforms, or other parallel systems). Often there are form factors with respect to modifying existing guidance systems that require unique computer hardware solutions.

There are components to the software design that require generic software libraries. A package that solves large sparse matrices can be used for mathematical model solutions. Software libraries that provide computer model mesh/grid generation are needed also (e.g. tetrahedral/hexahedral mesh generator). There are some standard mathematical libraries that are used too. Finite element models, and algorithmic components have also been designed. Once the preoperative phase has been completed, the computer model as well as any other information important for correction is either resident, transmitted, or manually loaded to an intraoperative computer controller.

When surgery begins, the intraoperative compute controller is activated. Custom-built software controls the compute controller and allows interaction with the image-guidance system via any type of network protocol to facilitate the transfer of intraoperative data to the controller (could be as simple as mounting of hard-drives via USB connection, or an onboard separate instantiated computer process on the guidance platform itself). During surgery, when data is collected from the guidance system, it is ported from the guidance system to the computer controller and the custom-built registration and deformation correction algorithm is invoked. The intraoperative compute phase begins with a registration between patient data as acquired by digitization equipment (e.g. optically tracked stylus, optically tracked laser range scanner, etc.) and corresponding data within the preoperative image set. This does represent a rigid registration. This transform is transmitted back to the IGS system if desired for a preliminary interrogation of the operative field by the surgeon while non-rigid correction is taking place.

Once the rigid registration is performed, the pose is used as an initial condition into the non-rigid correction. The correction is conducted in an iterative fashion with each iteration involving a nonrigid fitting phase followed by a re-establishment of boundary conditions done repetitively until the error between surfaces is below a given tolerance, meets a desired number of iterations, or continued fitting results in no improvement.

Upon completion of the nonrigid fitting of the preoperative image organ geometry to the intraoperative state of the organ, a local transformation process is initiated. This process involves calculating a voxel-by-voxel deformation map for every voxel within the organ domain moving from deformed space to undeformed space. Upon completion, an encompassing image mask is calculated around the deformed geometry. The deformation map is then allowed to diffuse out away from the surface to generate a mapping envelope to allow for a smooth local transform when a stylus is used within the IGS system.

Upon completion, the local transformation deformation map is transmitted to the IGS system. On the IGS system, as the localizer is used in close proximity to the organ, the undeforming voxel-by-voxel map is polled and the proper corresponding slice is displayed on the IGS display. More specifically, the local transformation provided acts to modify the location of any digitizer on the image-guidance display such that deformation is properly accounted for in determining the digitizer location within the image display itself. Alternatively, the local transformation can be applied to the image domain itself and modification of the image display can be achieved such that digitizers when rendered in the guidance display will interact with an altered image domain that is reflective of surgical conditions, i.e. a deformed preoperative image volume.

There is currently no commercially available image-guided system that accounts for deformation using this technology. There are several research groups that are undertaking similar research. With respect to the approach, it can be applied to specific organs as the software/hardware solution can be altered for different organs. The framework conceptualization has been realized in this document for accounting for intraoperative liver deformation. It could be adopted to brain, kidney, breast, etc. readily—so specification for organ type would be important. With respect to adoption, what is particularly nice about this approach is that it is adaptable to any guidance system with minor modifications.

A general flow of an exemplary method of the various embodiments is illustrated in FIG. 1. FIG. 1 is a flowchart showing steps in an exemplary method for performing an IGS procedure in accordance with an embodiment of the invention. As shown in FIG. 1, the method 100 includes a preoperative phase at block 102, an intraoperative rigid alignment phase at block 104, and an intraoperative non-rigid alignment phase at block 106. Following or concurrently with these phases, the IGS procedure can be performed at block 108.

As described above, the method 100 begins at block 102. At block 102, preoperative tasks are performed. The preoperative tasks include building a computer (i.e., mathematical) model of at least the soft tissues, organs, or other non-rigid structures of interest in the patient. Although the various embodiments of the invention will be described with respect to IGS procedures for non-rigid structures, the invention is not limited in this regard. Rather, the various embodiments of the invention are equally applicable in IGS procedures involving one or more rigid structures in a patient (e.g., bones) or a combination of rigid and non-rigid structures.

The computer model can be built using several sets of preoperative data. For example, preoperative images of the non-rigid structures are acquired and processed to generate a computer model that describes at least the geometry of the non-rigid structures of interest. These can be acquired using two or three dimensional imaging techniques. For example, some imaging techniques include computerized tomography (CT), magnetic resonance (MR), and ultrasound imaging techniques, to name a few. However, the various embodiments of the invention are not limited in this regard and any other imaging techniques can be used. Further, the computer model can also be configured to include any other possible data, such as physical data (e.g., elastic properties, thermoelastic properties, etc. and other aspects relevant to the mechanics of the non-rigid structure) that could be necessary to calculate deformation within the operative environment. Based on the data obtained, tasks for building the computer model can be performed. For example, a distribution of deformation shapes to be used in the fitting process can be generated. Also, preoperative image analysis can be performed in order to enhance feedback or computer mesh generation. Further, pre-operative generation of mathematical functions to assist fitting can be performed. Also, a designation/segmentation of shapes or partial surfaces of the non-rigid structures of interest can be performed. However, the invention is not limited in this regard and other tasks can be performed to enhance the imaging or fitting processes of method 100.

Although the various embodiments will be described primarily with respect to surfaces of non-rigid tissues that are exposed during medical procedures, such as the exterior surfaces of organs, tumors, and other biological tissues, the various embodiments are not limited in this regard. Rather, a "surface", as used herein, can refer to either external or internal features associated with a non-rigid structure of interest. That is, in addition to external surfaces, the surfaces referred to herein can include internal surfaces or features defined by a boundary between different structures or different types of tissues. For example, a boundary or division between cancerous and healthy tissues can define a surface. In another example, the division between liver vasculature and a parenchyma of a liver can also define a surface. In another example, it could represent the surface or feature point of a synthetic structure inserted within the organ that can be located via some localization method.

In the various embodiments of the invention, this preoperative phase can either be performed on one or more computing systems. Further, the preoperative phase can be performed on the same or different computing systems as the intraoperative tasks described below are performed. An exemplary computing system could include software packages configured to solve large sparse matrices that can be used for mathematical model solutions. Such a computing system could also include software libraries that provide computer model mesh/grid generation. Further, such a computing system can include both standard and customized mathematical and simulation libraries. Once the preoperative phase at block 102 has been completed, method 100 continues to block 104.

At block 104, intraoperative rigid alignment tasks are performed. That is, intraoperative surface data for one or more portions of the non-rigid structures is obtained intraoperatively and the counterpart surface data within image-space is obtained and aligned with a mathematical transformation. Thereafter the surface data of the non-rigid structure and the computer model are initially aligned. In some embodiments of the invention, a best-aligned method can be used. As used herein, a best-aligned method is an alignment of the image data and the non-rigid structures so that features on the surface of the non-rigid structure are positioned as close as possible to their image-space counterparts after the conclusion of the alignment process. However, the various embodiments of the invention are not limited in this regard and other alignment schemes can be used as well as internal substructures or feature points. Once this rigid alignment is complete, the surface data and the computer model are aligned, without any deformation of the computer model, i.e. a rigid alignment. Such an alignment can be performed in a variety of ways. For example, an iterative method can be use to alter the position of one of the surface data and the computer model until an error between the surface data and the computer model is minimized.

Additional processing of the available geometric surface data can also be performed at block 104. Intraoperative surface data can be obtained in a variety of ways. For example, some methods include ultrasound, MR imaging, CT imaging, laser and/or other light-based strategies, swabbing with a tracked stylus, to name a few. However, the various embodiments of the invention are not limited in this regard and other methods can be used to obtain surface data. In many cases, the surface data obtained will only represent a portion of the non-rigid structure, i.e. a partial surface. For example, during a liver procedure, only the anterior portion of the liver may be exposed. Therefore, the surface data could be acquired using laser range scan technology which would limit geometric data to representing the anterior portion of the liver. In another example, the liver and a tumor may be partially exposed. However, the surface of interest may be a boundary between a tumor and the liver, an interior surface. In such cases, ultrasound imaging could be used to locate such interior surfaces of interest.

The surface data can also include noise or other errors that could affect alignment. Accordingly, in some embodiments of the invention, once the surface data is acquired, the surface data can be filtered or otherwise processed to reduce or eliminate of noise and/or other artifacts. Such methods are well known to those of ordinary skill in the art and will not be described here. In the various embodiments of the invention, such processing can be performed before or after the rigid alignment. In addition, in some cases where multiple surface data acquisitions from different methods are available and digitized in a common coordinate space, a composite surface can be used for alignment purposes.

Upon completion of the rigid alignment at block 104, an initial correspondence function is generated that associates each point from the surface data with a counterpart point on the non-rigid structure within image-space. That is, for each point in the surface data, a means is provided for identifying the corresponding point in the computer model. For example, a closest point operator can be used to select the point on the computer model that is closest to each point on the surface data. In the various embodiments of the invention, this correspondence function may be expressed as a table, a mathematical function, or any other method of describing a relationship between the spaces defined two sets of points. In some cases, the deformation observed in the surface data may result in the correspondence function associating points from non-corresponding surfaces of the computer model with points on the surface associated with the surface data. Accordingly, in some embodiments of the invention, the closest point operator can be refined or constrained to limit its search to corresponding surfaces. That is, the computer model and the surface data can be associated with designators that differentiate between the various surfaces of the non-rigid structure of interest. Accordingly, the search for corresponding points can be limited by such designators. For example, anterior surface nodes of surface data could be limited to the anterior surface nodes of the computer model, despite the fact that posterior surface nodes of the computer model are closer.

For purposes of obtaining a correspondence function, the various embodiments of the invention are not limited to closest point operator methods. Rather any other methods for obtaining correspondence or registration functions between two surfaces can be used in the various embodiments of the invention. For example, in some embodiments of the invention, corresponding points can be selected using a ray projection technique in which a ray is projected along a line perpendicular to a point on one surface and the corresponding point is selected to be the point that is intersected on the second surface.

Once the rigid alignment and a correspondence function are obtained at block 104, method 100 can proceed to block 106. At block 106, a set of boundary or point (internal and/or external) conditions, based on the rigid alignment at block 106 and the correspondence function of 104, and a displacement field of vectors in three dimensions is iteratively computed to perform a non-rigid alignment of the computer model to the surface data. That is a displacement field of vectors for deforming the computer model to fit the surface data is computed. The operations occurring in this block will be described below in greater detail. Once the non-rigid alignment tasks are completed at block 106, the IGS procedure can be performed at block 108.

With respect to the design for implementing the method of FIG. 1, some embodiments can be embodied as a computer program product within a hardware controller or a combination of software and hardware components defining a controller. For example, the Stealth Model No. LPC-650-T9500-64GF-04G-6-E-00 Little PC (Computer) can be used in particular embodiments.

Figure 2:
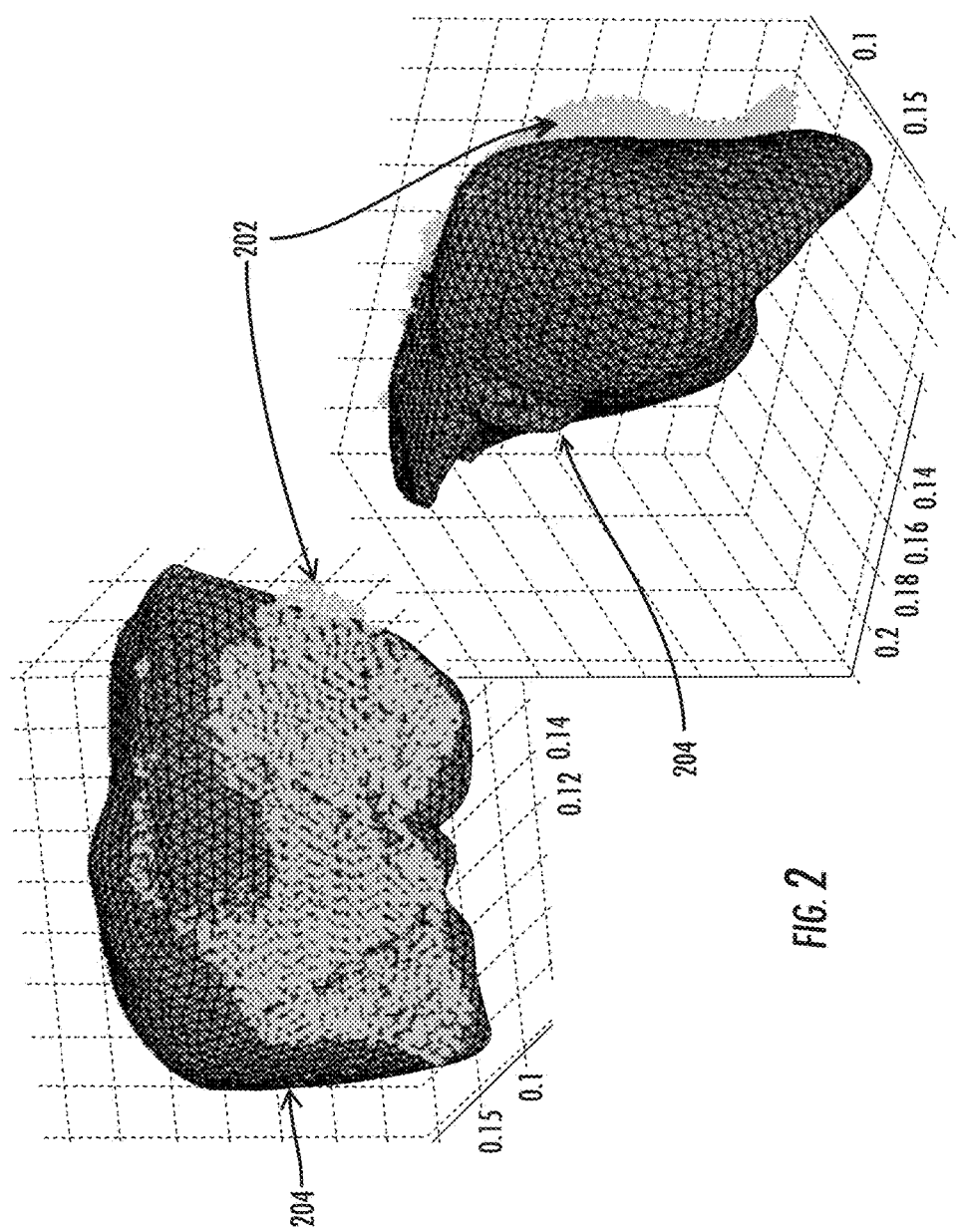
FIG. 2 illustrates front and back views of a result from a patient-to-image registration result using a salient feature weighting.
Figure 3:
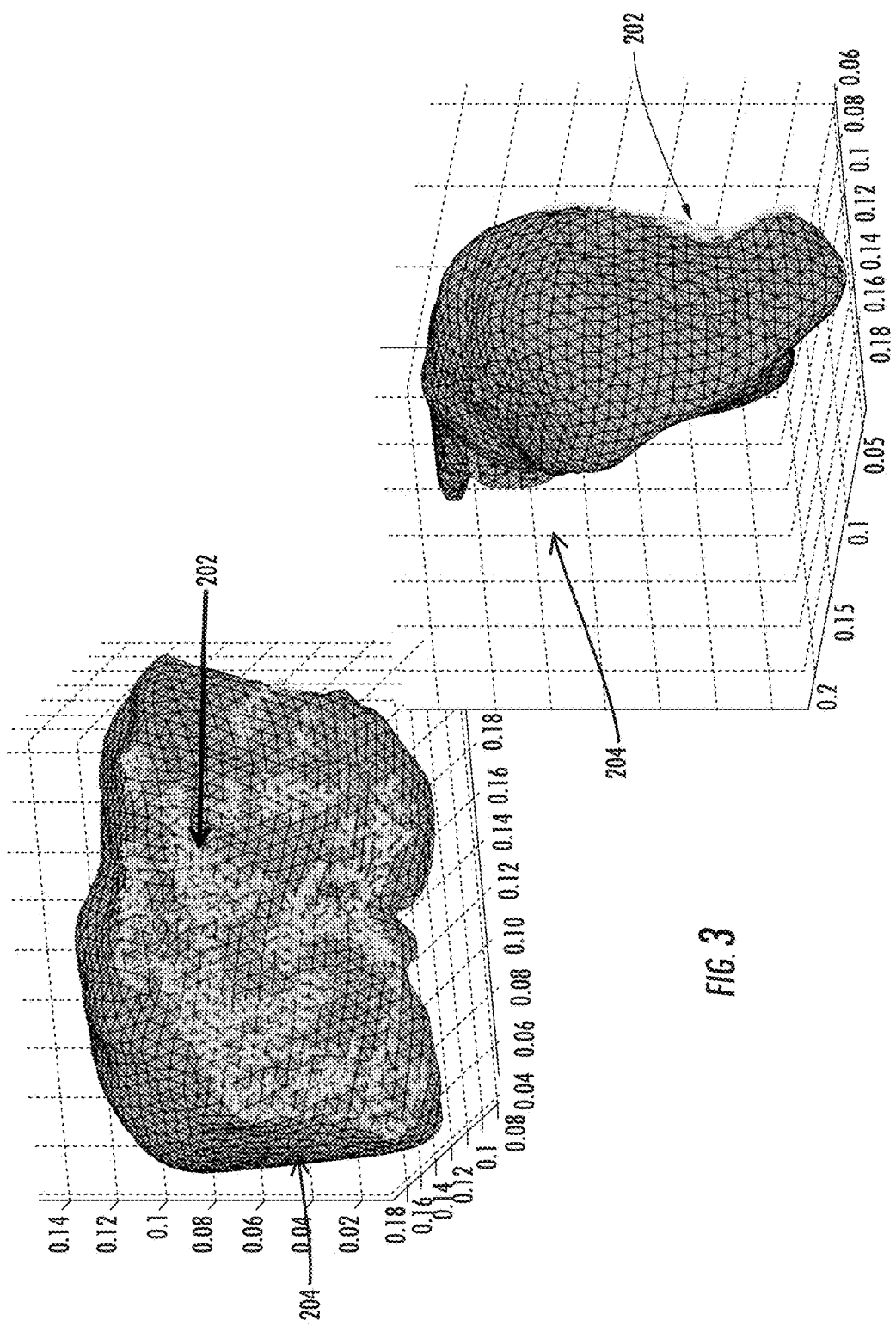
FIG. 3 illustrates the result after the registration is complete (via deformation of the computer model) with respect to the same data in FIG. 2.
Figure 4:
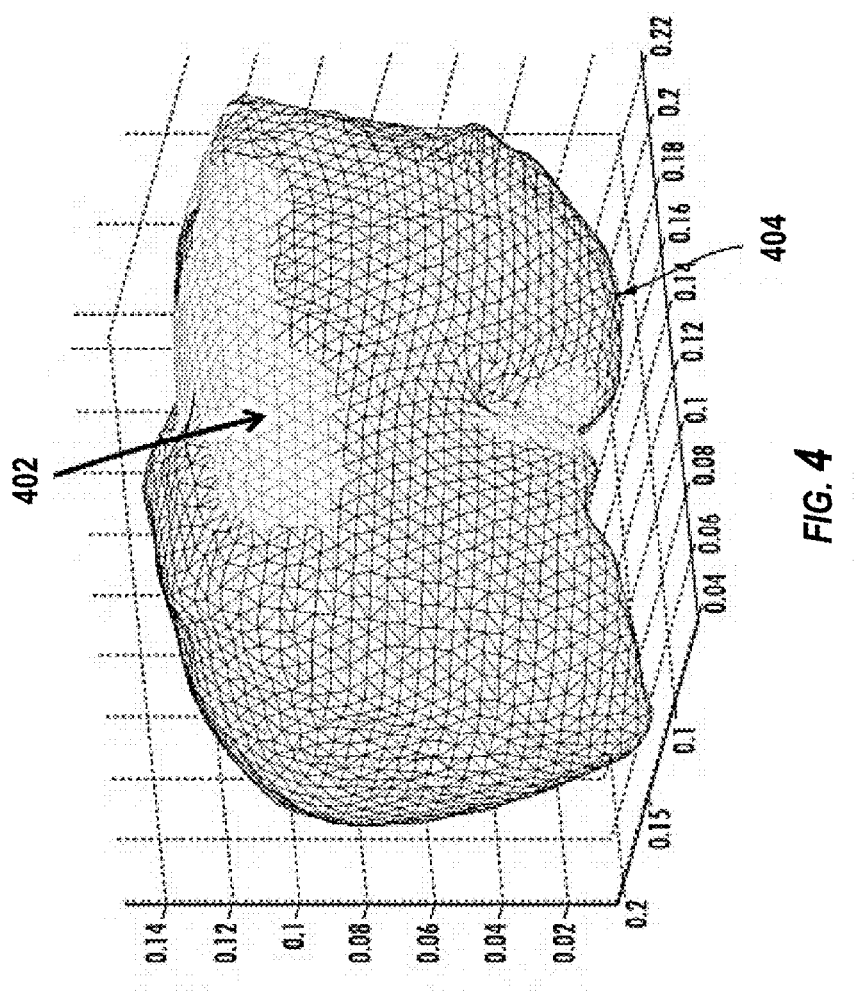
FIG. 4 illustrates an overlay of the non-deformed and deformed surfaces.
Figure 5:
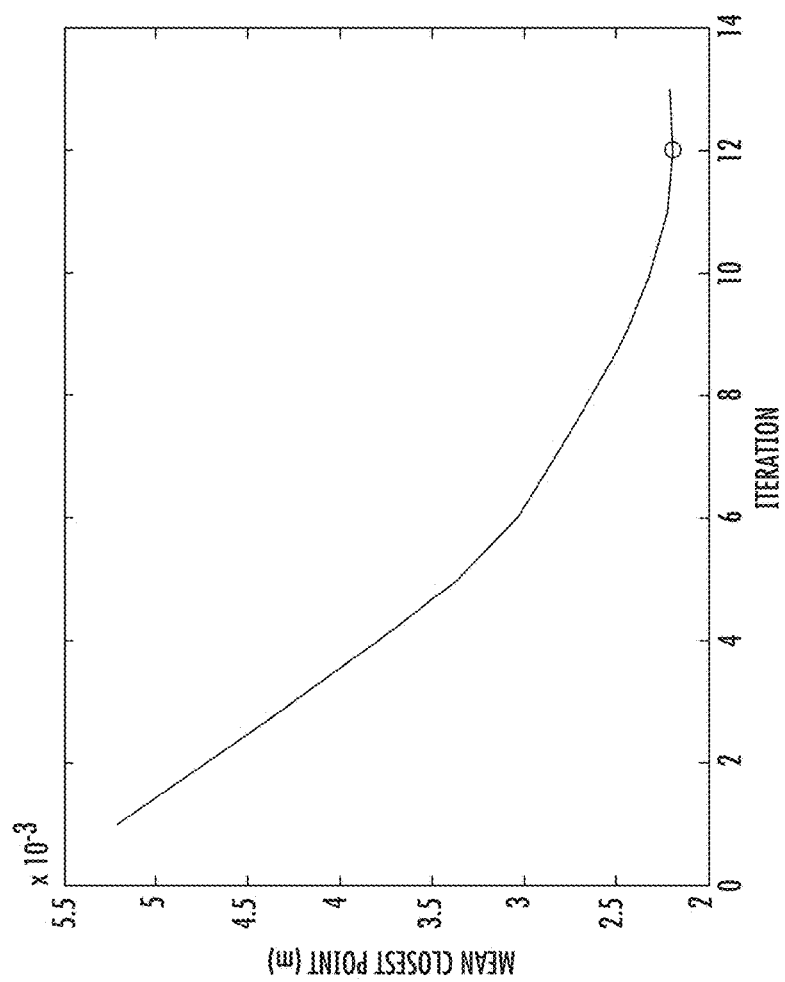
FIG. 5 shows the nonrigid convergence graph.

As an example of the achievable results of the various embodiments is presented in FIGS. 2, 3, and 4. FIG. 2 illustrates front and back views of a result from a patient-to-image registration result using a salient feature weighting. However, the various embodiments are not limited in this regard and alternate registration methods for an initial pose can also be used. For this example, the patient data (cloud 202) was acquired using a laser range scanner which is currently part of the guidance system versus a computer model 204 of a patient organ. Alternate methods of capturing organ geometry could be possible (e.g. stereo-pair, swabbing with tracked stylus, etc.). Once the initial pose is locked in, the non-rigid deformation algorithm begins. FIG. 3 illustrates the result after the registration is complete (via deformation of model 204) with respect to the same data in FIG. 2. FIG. 4 illustrates an overlay of the non-deformed (402) and deformed (404) surfaces and FIG. 5 shows the nonrigid convergence graph.

Figure 6A:
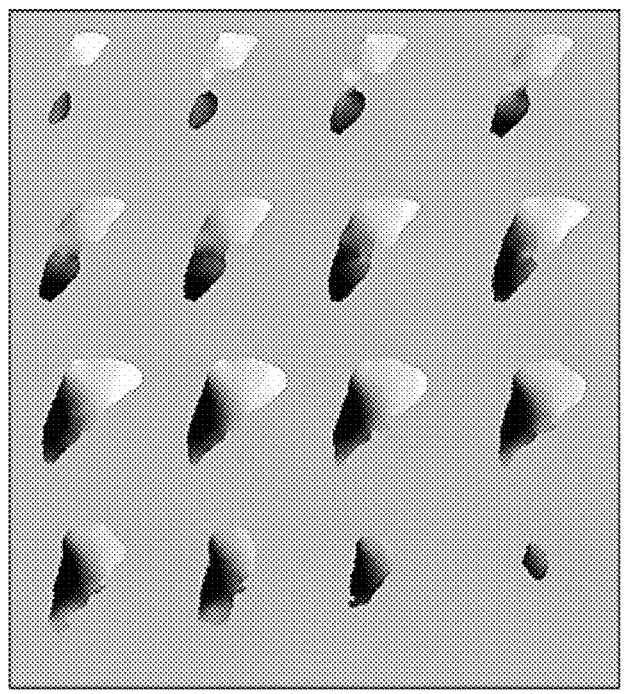
FIGS. 6A and 6B illustrate an example of the local transform for the 'y' coordinate associated with correction.
Figure 6B:
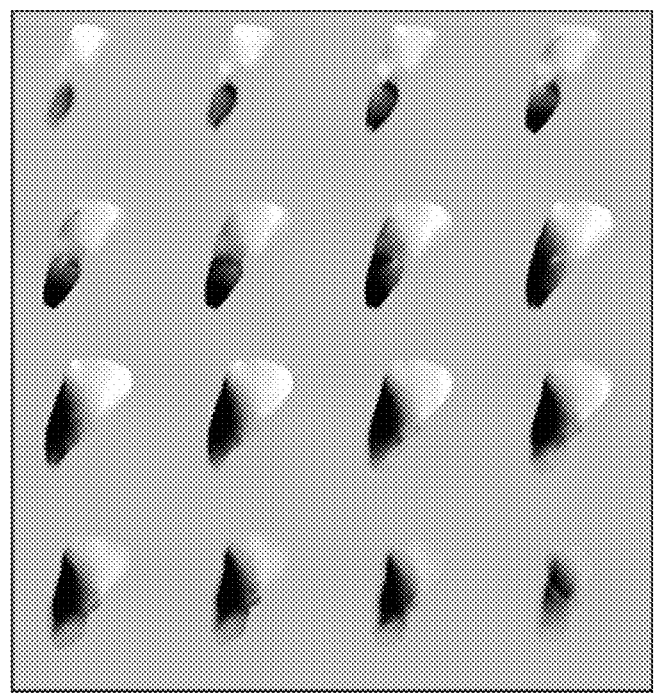

Once the transform is generated, a process of generating a local stylus transform is enacted. This is a local nonrigid transform (hence the title of the tech-transfer document) that provides a mapping from the stylus in patient-space to its appropriate position in image space. Typically this map will consist of 3 individual local transforms volumes (change in x, y, and z position in image space). Using this adjustment, the cursor can be moved in image-space to the appropriate image coordinate such that the proper image slice rendering is generated. FIGS. 6A and 6B illustrate an example of the local transform for the 'y' coordinate associated with correction. FIG. 6A shows the local transform map for one of the Cartesian directions for all points within the organ domain. The grayscale distribution represents a distribution of shifts in the 'y' direction based on the non-rigid correction. It should be noted that similar type maps are generated in the other two Cartesian directions thus provide a fully three-dimensional local transform. FIG. 6B shows the application of a diffusive filter to FIG. 6a to generate smooth local transforms for the stylus as it approaches the organ of interest.

Figure 7:
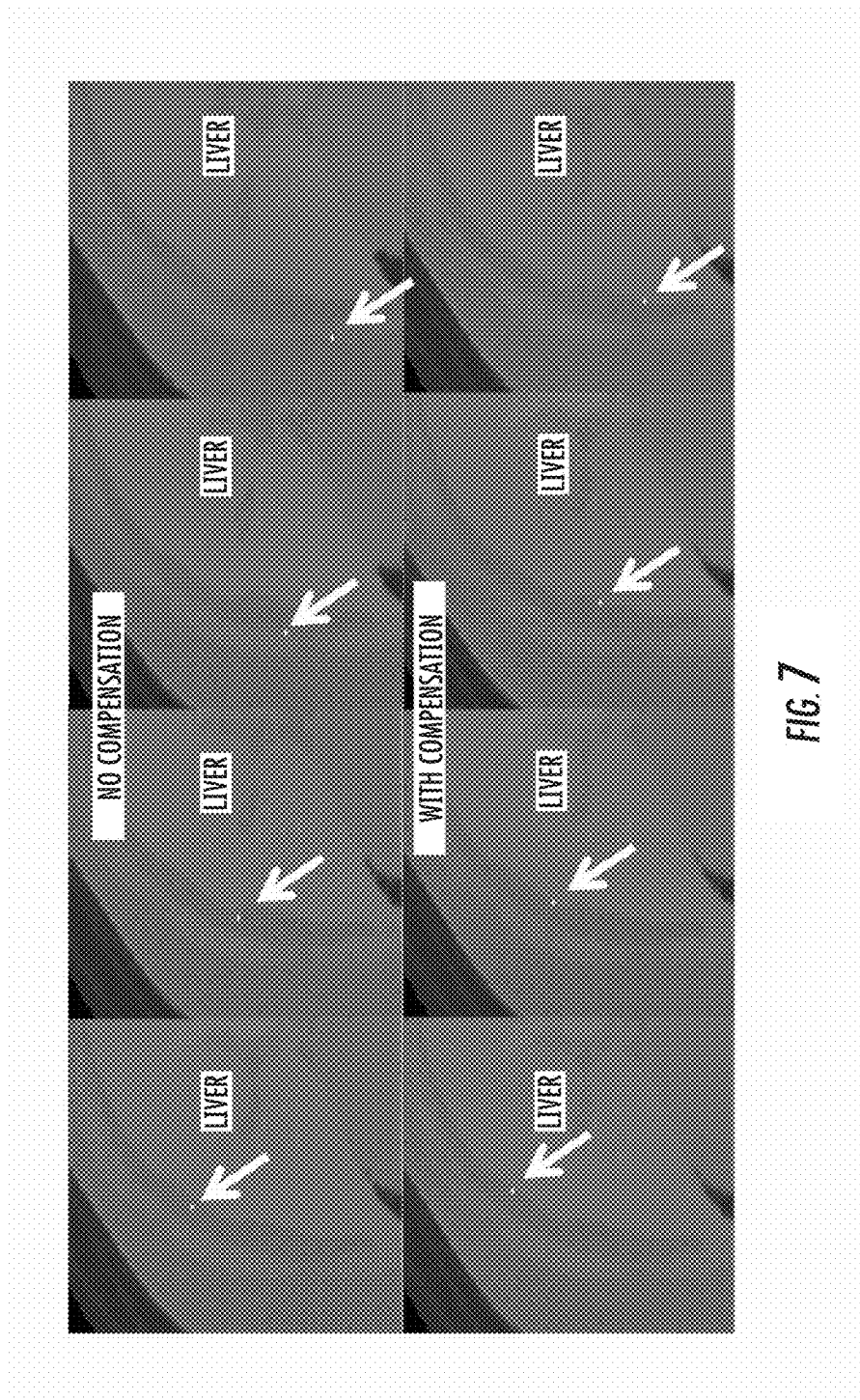
FIG. 7 illustrates an image-guided surgical process with and without compensation.

Upon generation of the full 3D local transformation mapping, this transform would be ported to the image-guided surgical system. The manner in which it operates is quite clear. As points are polled by the digitization technology in the patient's frame of reference, the local transform is polled and the appropriate shift is designated. Once designated, the proper cardinal image planes can be brought up on the IGS display and the surgeon gets a more accurate understanding of location. FIG. 7 illustrates this process whereby an image slice from the transverse plane through liver is polled based on using the rigid image-to-patient registration (equivalent to the registration results of FIG. 2 above).

In the top row of images of FIG. 7, a conventional rigid-registration method was used to align intraoperative organ and preoperative organ. The white cursor indicates the probe position as rendered on the images using the rigid patient-to-image alignment. Despite the stylus being dragged across the physical organ, notice how the cursor falls off the organ due to non-rigid deformation effects. In the bottom row of images in FIG. 7, the IGS cursor position is adjusted using a local stylus transform based on the non-rigid correction controller of the various embodiments. This shows a significant improvement in cursor position with it adhering to the contour of the organ (liver in this case).

In the various embodiments, the boundary conditions have been parameterized in a continuous functional form which allows for a reduced order determination of shape, i.e. less unknowns with more natural deformation transitions between regions of the liver. In addition, as opposed to the realizations in Miga. which began with establishing boundary conditions on the model in regions where correspondence was established from the registered laser range scan of the physical liver surface to the model, this new realization allows for boundary conditions to be specified on the posterior side (opposite side to the laser range scan acquisition) of the model such that the model's anterior side (side of the liver that laser range data is usually available) deforms (in reaction to the posterior boundary conditions) to match the intraoperative liver shape as recorded by the laser range scanner.

Put more simply, one allows the methodology to have the freedom to deform any surface on the model to match the shape of the intraoperative liver as defined by the laser range scanner. In Miga, one typically used the corresponding areas after the registered laser range data to initially drive the boundary condition determination. This represents improvements to the approach of Miga.

The goal of the approach of the various embodiments is to align the volumetric organ model (built from the preoperative image set) with the incomplete geometric patient data gathered intraoperatively. The basic structure of the algorithm is depicted by the flowchart in FIG. 8. A set of parameters described in the following sections is used to define the rigid and nonrigid components of a trial displacement mapping at each iteration. The algorithm initializes these parameters via a rigid registration and calculates the error between the model surface and the data at each iteration, updating the guess for the parameters using a nonlinear optimization routine until the surface fit is sufficiently accurate.

Figure 9:
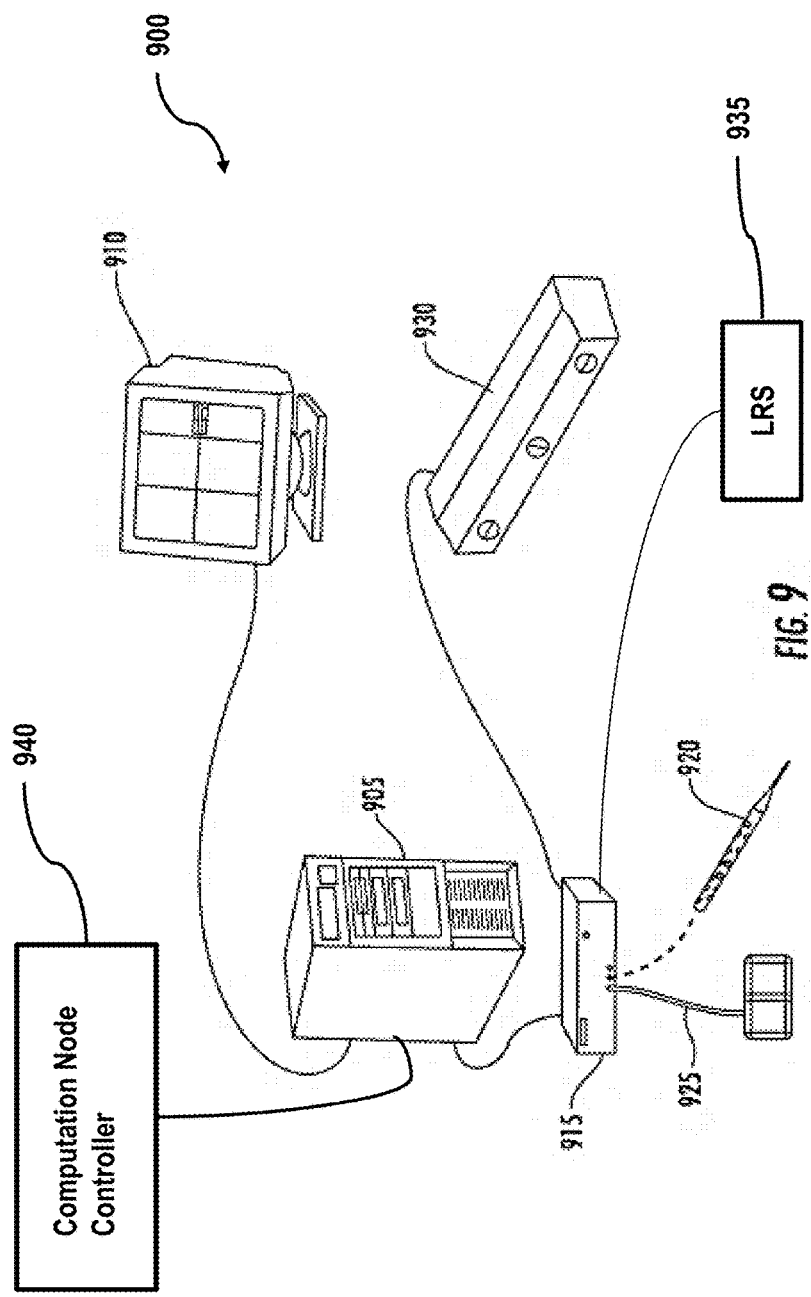
FIG. 9 shows an exemplary hardware system configuration in accordance with an embodiment of the invention.

An exemplary hardware configuration for performing one or more of the tasks identified above with respect to FIG. 1 is shown below in FIG. 9. FIG. 9 shows an exemplary hardware system configuration 900 in accordance with an embodiment of the invention. As shown in FIG. 9, system 900 can include an image/data processor 905, a display monitor 910, and an IGS controller 915. The IGS controller can be coupled to an optical tracking sensor which consists of sensing optical cameras 930, and emitters 920, 925, and 935. Further, the IGS controller 915 can be coupled to one or more emitters that can serve as instruments such as 920 and 935. 940 is a separate computation node controller that interfaces to the image/data processor 905 for the purpose of non-rigid deformation correction and the embodiment of related processes Although the various components are shown as separate, discrete components, the invention is not limited in this regard. For example, the IGS controller 915, the image data processor 905, and the computation node controller 940 can be integrated into a single system. Similarly, depending on the nature of correction, the computation node controller 940 could be separated into multiple computation node controllers networked together.

System 900 operates as follows. First, emitter 925 is often affixed to the patient or supporting surgical instrumentation. This could be replaced by providing a fixed camera mount (i.e. fix 930) within the operating room. Sensor 930 is used to determine the location of all emitters within the operating room (to include optical stylus 920, or potentially a laser range scanner 935). Emitter 920 or 935 could be used to detect a surface, or visible structure of a non-rigid organ or the location of an instrument. However, the invention is not limited in this regard and more than one sensing system can be used to provide surface data and/or instrument/object position data. An example of a system for generating surface data is a laser-range scanner system, such as the RealScan 3D system produced by 3D Digital Corporation of Danbury, Conn. or a similar system custom designed by Pathfinder Therapeutics Inc. of Nashville, Tenn. Such systems are capable of capturing three-dimensional topographic surface data as well surface texture mapping using an array of data points. For example, in one embodiment a scanning field of 500 horizontal by 512 vertical points can be acquired in 5-10 seconds and used to generate surface data of exposed surfaces during IGS procedures. In some embodiments, such a system can be tracked in the operating room space using a digitization system and calibrated using phantoms with separate independent digitization. 935 would represent the result of their use. One advantage of this laser-range scanner system over other surface digitization techniques is the capability of capturing feature-rich texture maps of the surface as well as the topographical characteristics. Such texture map data generally facilitates the segmentation, i.e. extraction, of the liver surface for alignment to preoperative imaging. Other embodiments could use a tracked ultrasound probe which could acquire external and/or interior surface data. The data could be used to extract any number of boundary data to include external and/or interior surface structures for use in the alignment process.

In operation, system 900 operates as follows. Prior to surgery, relevant data regarding the preoperative organ 102 would be transmitted to the computation node controller 940 or would have been processed on the controller 915. Upon collection of surface data from digitization equipment like that of 920 and 935, the image/data processor 905 transmits that data as well as any other relevant intraoperative information to the computation node controller 940. Using the computer model, the computation node controller 940 completes the rigid alignment of the computer model to the surface data and followed by the non-rigid alignment of the computer model to the surface data, as described herein. Data/image processor 905 may also perform transformations on the data. As described above, a local transformation may also be required. In such cases, the computation node controller 940 can generate such deformed and adjusted maps, as described above with respect to FIG. 5. The map can then be used to perform IGS procedures either by transforming points on the computation node controller 940, or by providing the proper mapping function to the data/image processing unit 905 and allowing it to apply the proper transform for the IGS display 910.

A. Overview of the Deformation Algorithm

Figure 8:
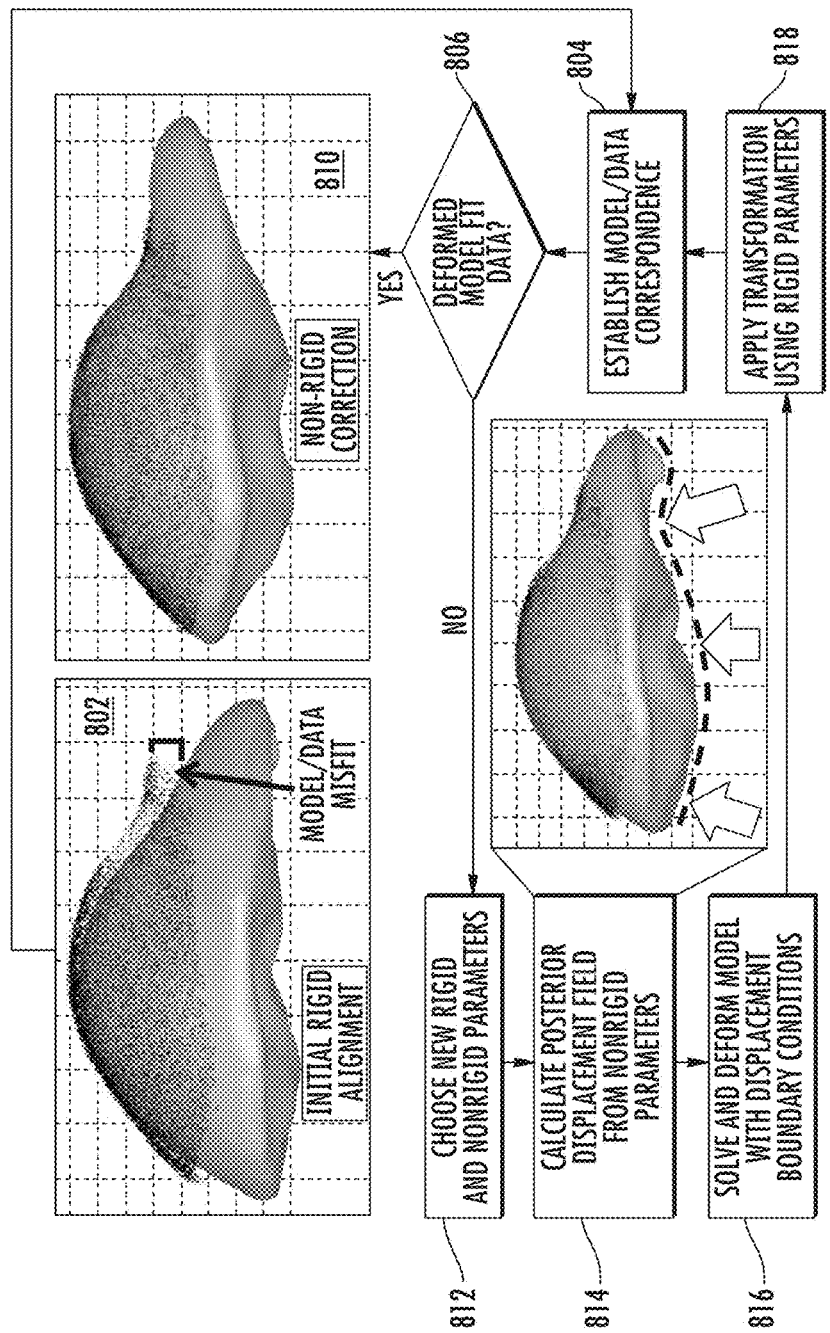
FIG. 8 is a flowchart showing steps in an exemplary method for computing deformation in accordance with an embodiment of the invention.

With respect to the non-rigid deformation algorithm used in this system, as illustrated in FIG. 8, the various embodiments may be described in the following list of steps taken by an algorithm in accordance with the various embodiments.

a. Perform an initial rigid alignment (Step 802 in FIG. 8).
b. Establish correspondence relationships between the surface data-points acquired intraoperatively and points on the surface of the computer model (Step 804 in FIG. 8). Correspondence can be based strictly upon mutual closest point relationships, or it may incorporate other geometric data such as the local normal vector direction or local curvature. The surface data-points provide an organ geometric representation, which in turn represents some form of spatial representation of the organ geometry of interest. For example, this could indicate three dimensional points in Cartesian space, a continuous or discrete representation of a surface, a series of continuous functional coefficients that define a surface, etc. Thus, the organ geometric representation computer model can indicate organ geometry information taken prior to the nonrigid process of interest (in this case surgery and usually taken from preoperative image data). Organ geometric representation data-points also can represent an organ geometric representation subsequent to a nonrigid change and acquired in some manner (e.g., using laser range scanning).

c. Determine whether there is a fit between the data-points and the model (Step 806 in FIG. 8). This includes computing a closeness metric for the entire dataset based on the 3D vectors which connect these corresponding points and other geometric features such as the surface normal (e.g. a closeness metric could be chosen as the sum of squares of the length of these vectors, or the sum of squares of the components of these vectors that are parallel to a vector normal to the surface of the computer organ model at each point a signed quantity. In the example below, the later metric is chosen.)

d. A set of deformation modes for a subset of the nodes can be established on the surface of the organ. This set of deformation modes may be parameterized in terms of a number of basis functions, in which case the deformation of the subset is completely defined by a finite number of coefficient values. In the example below, the nodes located on the "posterior" or backside of the surface were chosen as the subset to be parameterized, and the basis functions were chosen as terms of a third order bivariate polynomial.

e. Using a nonlinear optimization framework, the coefficient values of the basis functions in order to minimize the closeness metric are chosen iteratively. The steps involved in this framework are as follows:
  i. Choose an initial set of coefficients and compute the deformation of the subset of surface nodes (Step 812 in FIG. 8).
  ii. Enforce these displacements via boundary conditions in the computer model (Step 814 and 816 in FIG. 8).
  iii. Solve the computer model to obtain the non-rigid deformation of the entire organ volume (Step 816 in FIG. 8).
  iv. Apply a transformation using the rigid parameters (Step 818 in FIG. 8).
  v. Establish correspondence between the data-points and points on the surface of the new deformed computer model (Step 804 in FIG. 8).
  vi. Evaluate a closeness metric between the deformed organ model and the surface data points (Step 806 in FIG. 8).
  vii. Evaluate termination criteria based on the history of the closeness metric. Terminate algorithm if satisfied (Step 806 in FIG. 8).
  viii. Update the current guess of the coefficients in order to lower the closeness metric and repeat steps b through e (Step 812 in FIG. 8). This involves the use of a specific way to compute the update. In the example below, the well-established Levenberg-Marquardt update procedure is chosen. This requires computation of a Jacobian matrix which may be computed by separately solving the computer model a number of separate time and subsequently employing a standard finite-difference routine. In the example below, a partial inverse of the computer model was obtained preoperatively in order to reduce the computational burden of these model solves.

f. After termination of the algorithm in (vi), the correspondences are determined once more, and boundary conditions on the rest of the surface nodes are applied in the computer organ model in order to eliminate any remaining surface fit error that the algorithm in step (d) could not.

B. Nonrigid Deformation

The nonrigid deformation modes are selected according to an assumed type of surgical presentation. One can designate a "support surface" region on the posterior side of the organ where contact often occurs during routine mobilization of the liver from its surrounding anatomy and subsequent "packing" of support material underneath it to stabilize its presentation. It should be noted that the extent and location of the support area can be approximately known in advanced based on a surgical plan, and that reasonably small deviations from this plan only slightly affect the performance of the approach, as demonstrated by the experiments described below. The geometry of the organ itself usually provides an intuitive way to select the support surface. For example, one can select the support surface in a manner consistent with a typical surgical presentation. As shown in FIG. 10A, on most of the surface there is a defined edge or corner where the anterior surface 1002 transitions into the posterior side 1004. The entire posterior side of the organ can be manually designated as the support surface using this edge as a boundary, and this is the approach used in the examples below. However, the various embodiments are not limited in this regard.

A smoothly varying displacement field for the designated support surface is specified via a bivariate polynomial form as follows:

$$u_s = \hat{n}_s \sum_{1 \leq i+j \leq n} c_{ij} t_1^i t_2^j \tag{1}$$

where $u_s$ is the displacement vector for a point on the support surface, $\hat{n}_s$ is the average unit normal vector over the designated support region (the area weighted average over the triangular boundary elements), and $t_1$ and $t_2$ are tangential coordinates of the point on the support surface (measured from the origin perpendicular to $\hat{n}_s$ in two orthogonal directions). Thus, the constant coefficients $c_{ij}$ define the nonrigid displacement field over the support region. The sum over $1 \leq i+j \leq n$ avoids redundancy with the subsequent rigid transformation by excluding the constant displacement mode, which is captured within a general rigid-body motion.

For the surface nodes located on the support region, the corresponding displacements given by (1) are assigned as model boundary conditions to obtain a system of equations in the form Ad=b. Thus, solving the model produces a displacement field consistent with the assumed support conditions.

The model response to each of the coefficients $c_{ij}$ may be pre-computed and stored in matrix M, where each column is a displacement vector $d_{ij}$ obtained by solving the finite element system with the right hand side vector computed assuming $c_{ij}=1$ with all other coefficients are zero. Because the exemplary embodiment employs a linear elastic model, the principle of superposition applies, and M can subsequently be used to rapidly compute the model solution for any combination coefficients as $$d = Mc \qquad (2)$$

where $c=[c_{01}\ c_{10}\ c_{02}\ c_{11}\ c_{20}\ \ldots\ c_{n0}]^T$ is the vector of coefficients.

C. Rigid Transformation

After solving the model, a rigid-body transformation may be applied to the deformed nodal coordinates via a homogeneous transformation matrix consisting a translation vector $t=[t_x,t_y,t_z]\in\Re^3$ is the translation vector and a rotation matrix $R\in SO(3)$ computed as the matrix exponential of a skew-symmetric matrix defined by a rotation vector $\theta=[\theta_1\theta_2\theta_3]\in\Re^3$ as follows:

$$R = \exp\left(\begin{bmatrix} 0 & -\theta_z & \theta_y \\ \theta_z & 0 & -\theta_x \\ -\theta_y & \theta_x & 0 \end{bmatrix}\right)$$

If after solving the model, the position vector of node i is $p_i$, then rigid transformation produces a new position vector $p^*_i = Rp_i + t$. Thus, after nonrigid deformation and rigid transformation, a vector of parameters which defines the total displacement field can be expressed as $$P = [c^T t_x t_y t_z \theta_x \theta_y \theta_z]^T$$

D. Optimization Algorithm

The registration method in the various embodiments is based on a nonlinear optimization framework where the aforementioned parameter set is iteratively chosen to minimize an objective function defined by a metric quantifying the fit between the deformed model and the available data.

In this study, the following objective is proposed, $$F = \frac{1}{N}\sum_{i=1}^{N}\left(\hat{n}_{ci}^T(p_{di} - p_{ci})\right)^2 + \alpha E^2, \qquad (3)$$

where $p_{di}$ is a 3×1 vector containing the Cartesian coordinates for the location of the $i^{th}$ point in the surface data cloud, $p_{ci}$ is the location of the corresponding point on the model surface (a discussion of how correspondence is determined is provided below), $\hat{n}_{ci}$ is a unit vector normal to the model surface at $p_{ci}$. E is proportional to the total strain energy stored in the nonrigid displacement field produced by the model solution (before the rigid transformation is applied), and is calculated as $E=d^T kd$. α is a weighting constant, so that the term αE is a regularization term that balances accuracy of shape matching and the distortion of the deformation field.

The nonlinearity in the optimization problem arises from two sources: (1) rigid-body motion is inherently nonlinear due to the rotational component, and (2) allowing the correspondences between the model surface points and the data to update as the optimization progresses. At each iteration, the corresponding model point to each data point is assumed to be the closest-point (using the Euclidean distance) on the displaced model surface (which is defined by the current set of parameters). Thus, the approach implicitly solves the data-to-surface correspondence problem simultaneously with the nonrigid registration problem.

There are many well established optimization methods suitable for updating the parameter set at each iteration of the algorithm. It was found that the Levenberg-Marquardt procedure worked well and it was implemented it for the phantom and clinical cases described below. With this method, the parameter update step is computed as follows $$P_{k+1} = P_{k+1} - (J^T J + \lambda \text{diag}(J^T J))^{-1} J^T r, \qquad (4)$$

where $$r = \left[\frac{\hat{n}_{c1}^T}{\sqrt{N}}(p_{d1} - p_{c1}), \ldots, \frac{\hat{n}_{cN}^T}{\sqrt{N}}(p_{dN} - p_{cN}), \sqrt{\alpha}E\right]^T$$

is the residual vector containing each of the error terms which are subsequently squared and summed in (3), $\lambda>0$ is the damping parameter which can be selected iteratively to achieve optimal performance or set to a constant, and J is the Jacobian matrix of partial derivatives $$J = \frac{\partial r}{\partial P}.$$

Thereafter, the nonrigid registration approach proceeds as shown in FIG. 8. First, a set of initial parameters is chosen. One can choose the initial nonrigid coefficients $c_{i,j}$ to be zero, and one can use a rigid registration method to obtain an initial guess for the rigid parameters $t_x$, $t_y$, $t_z$, $\theta_x$, $\theta_y$, $\theta_z$. One method of initializing the algorithm is using the iterative-closest-point variant studied in [1]. However, any rigid registration method can be used for initialization, and even a non-optimal approximate alignment may be sufficient. The effect of perturbations on the initial registration is shown below. At each iteration, the algorithm then calculates the deformed nodal locations from using the nonrigid coefficients. The transformation defined by the rigid parameters is then applied to the deformed nodal coordinates to produce the final displacement field for the iteration. Correspondence between the model surface and the data is then via closest point relationships and the residual vector function is evaluated. One can compute the Jacobian matrix J via finite differences by evaluating the residual vector for small changes in each parameter, and apply the Levenberg-Marquardt update step to calculate the next guess for all parameters. This process is repeated for a fixed number of iterations (10 used in the experimental trials) or until the surface fit is sufficiently accurate.

E. Incorporating Model Modifications

In general, it is straightforward to adapt the proposed modeling approach and optimization framework to include deformation effects from a variety of sources other than normal displacements on the support surface, by simply parameterizing them within the elasticity model of the organ. For example, tangential displacements on the support surface can be parameterized in exactly the same way as the normal displacements in (1). This could be useful if the expected surgical presentation involves "unfolding" the liver or stretching it out on the support surface before resection. In addition, distributed tissue forces arising from gravity (due to orientation changes) or fluid perfusion can be modeled if they are expected to play significant role in the organ deformation.

As an example, consider including gravity g as a force distribution vector which is constant over the volume. When building the finite element system in Equation (2), the right hand side vector f is linear in the components of g, and the matrix K is unaffected. Therefore, the model response to each gravity component can also be precomputed and stored as an additional column of the matrix M used for fast model computation in (5). Then one can simply include the components of g in the parameter vector P so that they are simultaneously selected with the coefficients $c_{i,j}$ and the rigid parameters within the optimization routine. The decision to include or not include a particular effect can be made based on the anticipated surgical plan and/or the nature of the intraoperatively acquired data, in order to balance trade-offs between concerns for computational speed, model accuracy, and over-fitting.

F. Incorporating Intraoperative Subsurface Data

In the case where additional subsurface data is available intraoperatively, e.g. a tumor location from tracked ultrasound measurements, one can modify the objective function accordingly, as $$F = \frac{1}{N} \sum_{i=1}^{N} \left( \hat{n}_{ci}^T (p_{di} - p_{ci}) \right)^2 + \alpha_1 E^2 + \alpha_2 \|p_d - p_c\|^2, \quad (5)$$

where $p_d$ is the location of the point of interest as measured intraoperatively, and $p_C$ is the location of the corresponding model point as predicted by the parameterized displacement field. The point of interest would need to be specified in the preoperative image set before this information could be included in the objective function.

Additional Features

First, rather than representing the boundary conditions as discrete kernels which can be updated a variety of ways, an approach may choose to parameterize the surface in a continuous, overlapping, or multi-domain coupled functional form. This provides a more continuous distribution of deformations than discrete kernels per se and could change the number of unknowns for establishing boundary conditions (e.g. reduce the number of unknowns to make the problem faster and more tractable).

Second, while model updates can be provided by varying kernels or parameters within a functional form, it may be advantageous to incorporate the modes of contributing deformations (i.e. the typical deformation field arising) from each kernel or parameter associated with the functional form into the iterative fitting process.

Third, the boundary conditions associated with the fitting process are prescribed on the organ geometry which could be represented as points, surfaces, spline coefficients, etc. The application of boundary conditions can be associated with any region of the organ, i.e. the application of boundary conditions is not limited to include only the geometric regions of the organ where corresponding intraoperative data is approximately known. More specifically, the method should not be limited to extrapolating to regions where correspondence is largely unknown and parameterizing regions where correspondence is approximately known. But rather, any representation of the organ geometry of the computer model can be parameterized for the determination of the boundary conditions, and likewise any representation of the organ geometry data can be utilized for the fitting or matching process provided some form of data/information regarding the misfit is provided. Information for the fitting process (i.e boundary conditions) can take on many forms—displacements, forces, geometric nonlinear constraints such as collision conditions, that is, essentially any measurable or behavior-based information associated with the deformation of soft tissue.

Finally, as this is boundary condition geometry based fitting/matching approach, any number of optimization methods can be used to address this process. In this realization a Levenberg-Marquardt scheme is used as an example which involves the calculation of a Jacobian matrix done in this case using a finite difference method. Essentially any optimization method that evaluates an objective function could be cast towards this approach.

The use of the proposed iterative method for nonrigid registration of the preoperative liver to the intraoperative environment is feasible to be incorporated into a surgical workflow with minimal encumbrance, and the experimental analysis below shows that the method significantly improves upon the robust rigid registration currently used in commercial systems, as well as previously investigated nonrigid methods. In addition, the method can provide fully realized for a sparse data acquisition environment thus potentially allowing for wide scale adoption by image-guided surgical platforms for soft-tissue organ guidance.

EXAMPLES

The following examples and results are presented solely for illustrating the various embodiments and are not intended to limit the various embodiments in any way.

A. Methods

The nonrigid registration algorithm is presented here as a central component in the context of a patient-specific data pipeline for surgical navigation. Prior to the registration realization, several data acquisition and processing steps were performed. The procedures described below were used in both the phantom experiments and the clinical examples presented herein.

B. Intraoperative Data Collection

The method of the various embodiments was evaluated by intraoperatively acquiring a set of 3D points corresponding to a portion of the organ surface. For this, a custom-built commercial laser range scanner (Pathfinder Technologies, Inc., Nashville, Tenn.) was used. Intraoperatively, once the organ is presented, the laser range scanner sweeps a laser line over the surface of interest and records both shape and color information, i.e. a textured point cloud. Using the color information from the field of view, the organ surface can be rapidly segmented leaving only the sparse liver geometrical data. Alternatively, surface points could be gathered via an optically tracked stylus which can be swabbed over the organ surface. Once intraoperative surface data are acquired, anatomical landmarks are designated from the data (e.g. falciform ligament, inferior ridges, round ligament) and a salient feature ICP method developed in [1] is used to obtain an initial rigid registration.

With respect to additional geometric information, intraoperative ultrasound is routinely used within liver resection surgery. In addition, recently commercial guidance systems have begun to integrate tracking information with the ultrasound to provide references between ultrasound and preoperative images (e.g. Pathfinder Technologies Inc. has a tracked attachment for a t-shaped ultrasound transducer). Given that tumors are often localized with ultrasound, it is conceivable that a tracked probe could be used to locate one or more points of interest inside the organ, e.g. a tumor centroid or large vessel bifurcation. The the effect of including such additional data in the phantom experiments discussed below in greater detail.

C. Finite Element Model from Preoperative Image Set

CT image volumes are typically acquired approximately one week prior to performance of the surgical procedure. For clinical cases, a a semiautomatic method of [2] and [3], based on the level set method proposed [4], to segment the liver from the surrounding anatomical structures in the preoperative tomograms. For the phantom cases studied herein, the liver surface was manually segmented using the ANALYZE software system, available from the biomedical Imaging Resource, Mayo Clinic) due to the ease of segmenting phantom data. Isosurfaces are generated from the liver segmentations via the marching cubes algorithm and smoothed via radial basis functions (RBF) (FastRBF toolkit, FarField Technology, Christchurch, NZ). A tetrahedral mesh is then generated from this surface using the customized mesh-generation software. Using a nominal tetrahedron edge length of 4 mm results in a triangular surface representation with a resolution such that discrepancies between the RBF and the surface mesh are minimal.

The linear elastic model entails the use of the standard 3D Navier-Cauchy equations for the displacement field:

$$\frac{E}{2(1+v)(1-2v)}\nabla(\nabla \cdot u) + \frac{E}{2(1+v)}\nabla^2 u + F = 0, \quad (6)$$

Where E is Young's modulus, v is Poisson's ratio, u is the 3D displacement vector at a point in the body, and F is the applied body force distribution. Using linear basis functions defined on the tetrahedral elements, one can perform the standard Galerkin weighted residual method to obtain the standard linear system of equations of the form $$Kd=f \quad (7)$$

where K is the 3n×3n global stiffness matrix, $d=[u_{1x}\ u_{1y}\ u_{1z} \ldots u_{nx}\ u_{ny}\ u_{nz}]^T$ is the vector of nodal displacements, and f contains the contributions of the applied body forces and/or surface tractions at each node.

Displacement boundary conditions are applied at a subset of the surface nodes by modifying the corresponding equations in (7), which results in a new system of equations, $$Ad=b \quad (8)$$

which is solved for the nodal displacements that satisfy static equilibrium for the given boundary conditions.

D. Experimental Validation Studies

The nonrigid registration method, as described above, was then evaluated in a series of experiments with anthropomorphic liver phantoms. The results of the method are compared to ground-truth fiducial locations throughout the phantoms as measured by CT imaging. First, to verify that the approach is broadly applicable, its accuracy is analyzed in four cases where a phantom underwent a set of plausible deformations ranging from small to large. The phantom used in these four cases contained 28 fiducial targets evenly distributed throughout its volume for validation.

Then, to provide a more detailed investigation of the limitations and sensitivities of the method, a number of analyses for a single additional large deformation case where the phantom contained a denser distribution of 58 validation targets are described. For this representative and data-rich case, evaluated are: (1) the additional accuracy of the nonrigid registration beyond rigid registration alone and previous nonrigid registration methods, (2) the result of incorporating subsurface data into the framework, (3) the result of employing a nonlinear corotational approach in place of the linear elastic model, (4) sensitivity analysis with respect to choosing of the number of modes and the energy weighting coefficient, (5) robustness analysis with respect to variations in the initial rigid alignment, (6) the result of incorrectly designating the support surface region, and (7) the result of having various extents of surface data coverage, from small to large.

E. Data Collection Procedure

A compliant liver phantom was made using a cyrogel of water, Polyvinyl alcohol, and glycerin. This recipe was refined based on knowledge of organ motion derived from a 75 patient multi-center clinical trial. Plastic target beads (visible in CT) were evenly dispersed inside the phantom to serve as ground-truth fiducials in the analysis. A CT scan of the phantom was taken to identify the initial target locations. The finite element model mesh was generated from this image volume representing the "preoperative", undeformed organ state. Next, the phantom was deformed by adding blocks of support material under certain parts of the posterior side of the liver, simulating the intraoperative procedure of organ repositioning and stabilization by packing material underneath. In this deformed state, surface data is captured with a laser range scanner (LRS) to drive the nonrigid registration algorithm, and a second CT scan was taken to identify the post-deformation target locations for validation. An initial rigid registration was acquired via the weighted patch ICP algorithm in. The nonrigid algorithm described herein was then applied to deform the model to match the surface data.

F. Results over a Range of Deformations

Figure 11A:
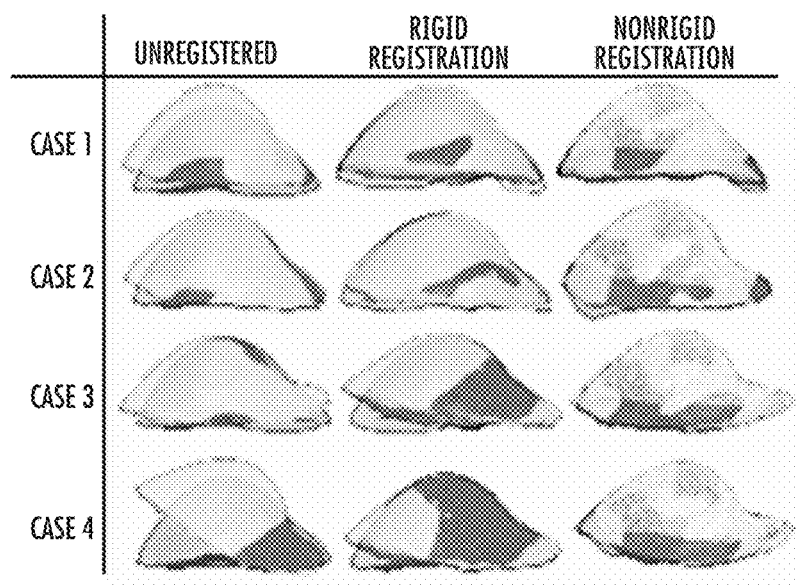
FIG. 11A shows the exemplary deformations evaluated and the resulting rigid and nonrigid deformations in accordance with the various embodiments.

To evaluate methods of the various embodiments over a range of deformations that could be encountered in surgery, the liver phantom was deformed in four different ways, as illustrated in FIG. 11A, by adding support blocks underneath various parts of the phantom. In case 1, two support blocks were added underneath the middle of the phantom, allowing the side lobes to droop. In case 2, a block was placed underneath the right lobe, and in case 3 a block was placed under the left lobe. In case 4, a block and an extra towel were placed under the right lobe, which gave rise to a significant rotational component in the displacement field as well as a sharp bend in the corner of the left lobe near the falciform ligament. Simulated intraoperative surface data was gathered by sampling the post-deformation CT surface. Salient features patches were designated and the weighted iterative closest point algorithm (wICP) studied in was used to obtain the initial rigid registration shown in the middle column of FIG. 11A. Then nonrigid algorithm described above was then applied to fit the model surface to the LRS data. The degree of the bivariate polynomial was n=3 (resulting in nine nonrigid parameters in addition to the six rigid parameters), and the energy weighting coefficient was chosen as $\alpha_1=10^{-9}\ N^2$ with a Young's modulus of 2100 Pa and Poisson's ratio of 0.45 in the elastic model. (Note that since the model contains no body forces and only Dirichlet boundary conditions, the value of Young's modulus does not affect the displacement solution, only the scale of the stored energy).

Figure 11B:
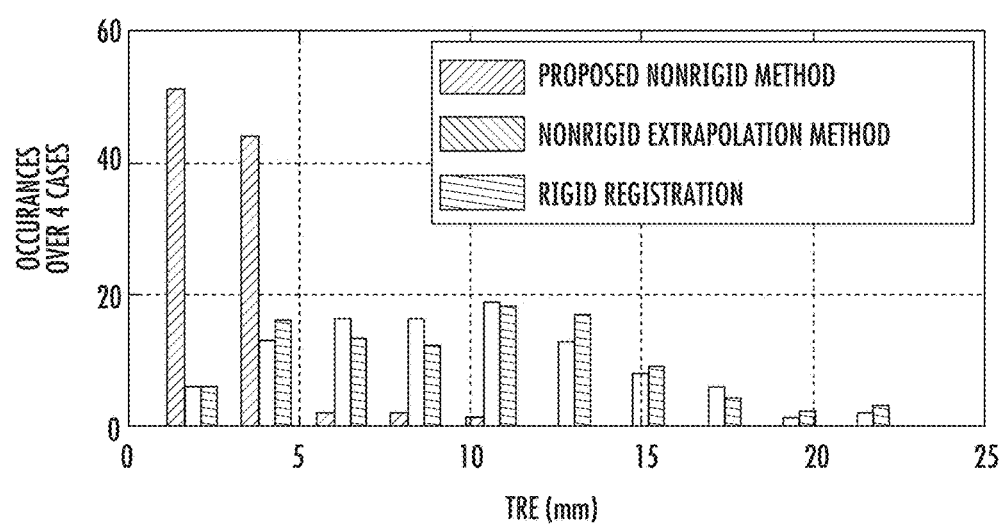
FIG. 11B shows a histogram plot of target registration errors for the cases in FIG. 11A.

A histogram of target registration errors (TRE) over the four cases using rigid registration, a previous nonrigid method, and the proposed nonrigid method for the various cases of FIG. 11A is shown in FIG. 11B. Over the 25 embedded target fiducials dispersed throughout the liver, the mean target registration error (TRE) after rigid registration was 9.5 mm, 13.8 mm, 7.9 mm, and 8.3 mm in cases 1 through 4 respectively. After applying the nonrigid registration algorithm, the mean target error was reduced to 2.7 mm, 3.0 mm, 3.2 mm, and 3.7 mm, respectively.

G. Comparison of Methods for a Representative Case

The same data collection procedure described above was applied to a liver phantom with 58 embedded target fiducials, which was deformed by placing support blocks under both left and right lobes as well as the front portion of the phantom. The extra support material caused significant upward displacement of the supported portions of the phantom, while the unsupported portions sagged down to the bottom of the container. This large deflection case with a denser distribution of fiducial targets is used to evaluate various aspects the method of the various embodiments in the following subsections.

Figure 12A:
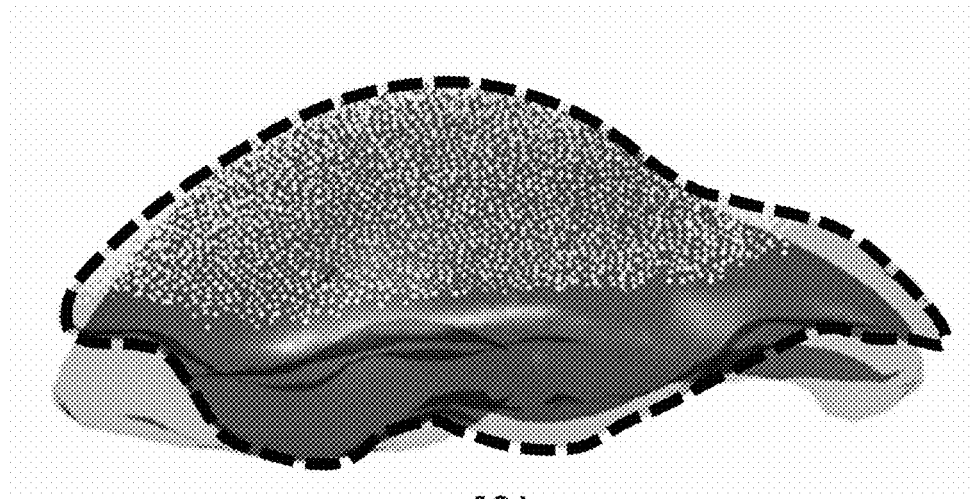
FIGS. 12A and 12B show LRS data cloud superimposed on the post-deformation CT segmented surface for an initial rigid registration and the iterative method of the various embodiments, respectively.
Figure 12B:
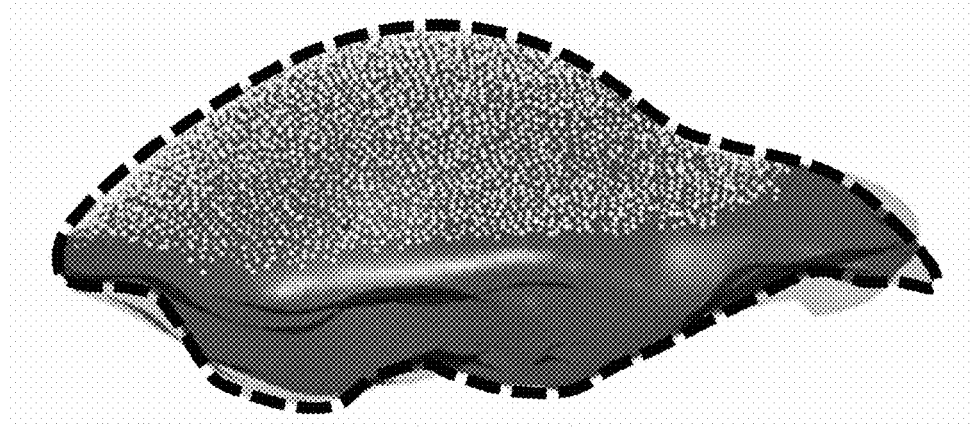

FIGS. 12A and 12B show the results for a rigid deformation according to [1] and the deformed model surface resulting from the algorithm, respectively. With the true deformed surface generated from the second CT scan highlighted using a dotted line. The deformed model in FIG. 12B visually matches the partial surface data as closely as possible and also displays the same qualitative behavior as the true surface in the posterior region where no data is present. The model predicts that the three supported sides are displaced upward as much as the true surface and the middle and back remain as low as the true surface.

Predicted post-deformation target locations were also generated using the algorithm's displacement mapping and compared to their CT-measured post-deformation locations to assess ground-truth accuracy.

Figure 13:
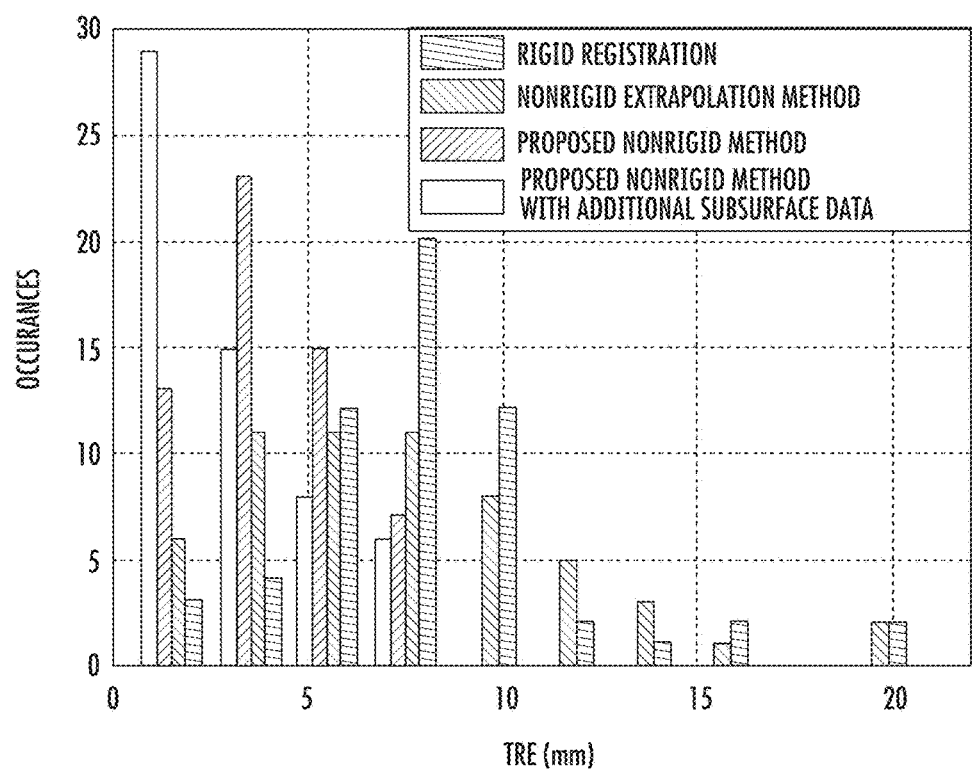
FIG. 13 shows the statistical information for 58 target locations across the three different registration methods for comparison.

FIG. 13 collects the statistical information for all 58 target locations across the three different registration methods for comparison. The rigid registration method of [1] (dark shaded) shows with a mean TRE of 8.0 mm. For completeness, the results for nonrigid method in Miga (lightly shaded) shows a mean TRE of 7.2 mm. The iterative method of the various embodiments (hatched) shows a mean TRE of 4.0 mm. The error distribution of this iterative method has less spread than the other methods indicating better agreement over a wider geometric region is being achieved.

H. Improvement Using Subsurface Data

To investigate the effect of incorporating of subsurface data (which could be acquired e.g. by identifying a subsurface feature using tracked ultrasound), a subsurface tumor was simulated by embedding a polyester sphere soaked in barium sulfate within the phantom. The pre- and post-deformation locations of the simulated tumor centroid were determined from the CT images and used as described in Section II as additional data in the fitting process with $\alpha_2=0.01$. Including this one additional subsurface data point improved the mean TRE to 3.3 mm, and the resulting TRE distribution is shown in FIG. 13 (no shading).

I. Robustness to Initial Registration

Also analyzed was the robustness of nonlinear optimization procedure to the initial registration input. In general, the data input to algorithm was assumed to be already rigidly registered (e.g., using the wICP algorithm in [1]) to provide a good initial estimate of correspondence between the model and the intraoperative surface data. To assess the role that small initial alignment variations might play during the course of the iterative nonlinear optimization process, a Monte Carlo simulation was performed where the initial alignment between the LRS point cloud and the preoperative liver model was perturbed in 6DOF space by a maximum total angle of 10 degrees and translated by up to 10 mm in each direction. In 100 simulations, all of the final mean TRE values fell between 3.6 mm and 4.4 mm which compares similarly to the 4.0 mm mean TRE obtained with the original wICP alignment.

J. Sensitivity to Weighting and Number of Modes

Also investigated was the sensitivity of algorithm to changes in the formulation of the optimization problem, namely the energy weighting coefficient $\alpha_1$ and the order of the bivariate polynomial which defines the displacement of the support surface. The resulting statistics for the target registration error (TRE) is summarized by the boxplots in FIGS. 14A and 14B. These are statistical boxplots illustrating the sensitivity of the results of the algorithm to changes in the weighting coefficient $\alpha_1$ and the order n of the bivariate polynomial for the support surface displacements. Once can conclude from inspection of the results that n=3 provides a sufficient number of support surface modes (9 modes) for accurate subsurface predictions, but increasing the number past this yields successively diminishing returns. Similarly, reducing the energy weighting coefficient will yield more accurate results up to a point.

The trade-off for decreasing $\alpha_1$ is that unrealistically large deformation predictions are possible if the chosen mode set cannot easily reproduce the surface data. This could be the case if the designated support surface was wildly incorrect or if there is significant unmodeled behavior such as swelling due to perfusion or transverse stretching of the organ. It should be noted that these types of behavior could also be parameterized and included within the framework, and the choice of modes should be refined over time according to experience and clinical case data. To buffer this uncertainty, $\alpha_1$ provides a way to control the amount of predicted deformation to a reasonable level. Upon collecting surface data, it can be increased if the deformation looks unreasonable.

K. The Effect of Incorrect Support Surface Designation

One potential limitation to the proposed method is that it requires an a priori assumption about what part of the organ surface is directly contacted by support material. Experience with image-guided liver surgery indicates that a good estimate of the actual support surface can be easily determined from the preoperative plan performed by the surgeon. The posterior region (1004) of the organ as shown in FIG. 10A is usually easy to manually segment by using the high surface curvature at the lobe edges as a boundary. This posterior region serves as an appropriate starting point for the support surface designation which can be modified according to the surgical plan if necessary.

Even with a good estimate of the support surface, accuracy of the nonrigid registration will no doubt be affected by the degree of agreement between this assumed support region and the actual intraoperative support region. To provide an estimate of how much an incorrect support surface designation might affect registration accuracy, the methods described herein were test under a case where the support region was quite incorrectly, as shown in FIG. 10B. The resulting mean target registration error for the incorrectly designated case was 4.6 mm, compared to a mean TRE of 4.0 mm in the correctly designated case. This result indicates that an accurate nonrigid registration may still be obtained even if the support surface designation is somewhat inaccurate.

L. The Effect of Data Coverage Extent

Figure 15C:
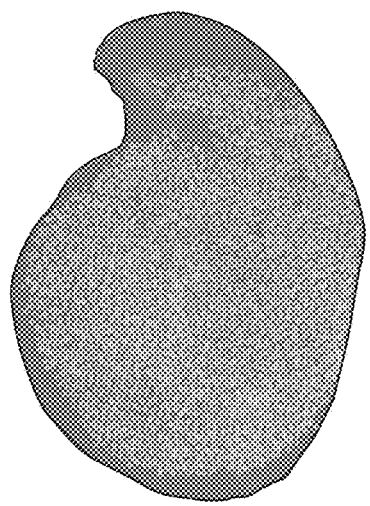
FIGS. 15A. and 15B, and 15C show different extents of surface area evaluated.
Figure 15B:
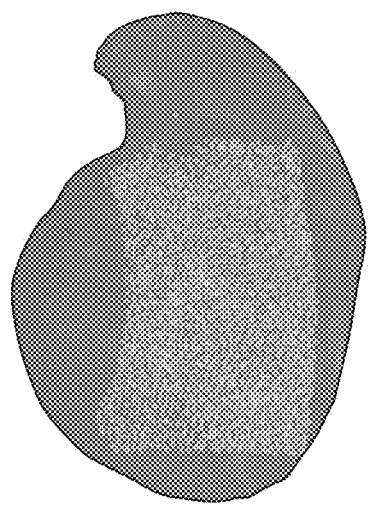
Figure 15A:
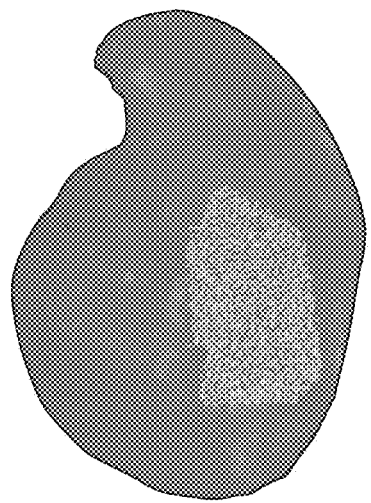

Also investigated was the effect of having smaller patches of intraoperative surface data available for registration. As shown in FIGS. 15A, 15B, and 15C, tested were three sizes of data coverage, the largest of which was the dataset used in the representative case. The resulting mean TRE for the two smaller extents (FIGS. 15A and 15B) was 5.0 mm and 5.2 mm respectively. The resulting mean TRE for the largest extent was 4.0 mm.

M. The Effect of Including Gravity

As discussed above, other forces on the tissue such as gravity are straightforward to include within the model and registration framework. Performed was an additional execution of the registration procedure for the case in FIGS. 12 A and B and gravity was included in the model and the parameter set to be optimized, as described above. The resulting TRE distribution was very similar to that shown in FIG. 13 obtained without including gravity, and the mean TRE was slightly decreased to 3.9 mm.

N. The Effect of Model Linearization

Figure 16:
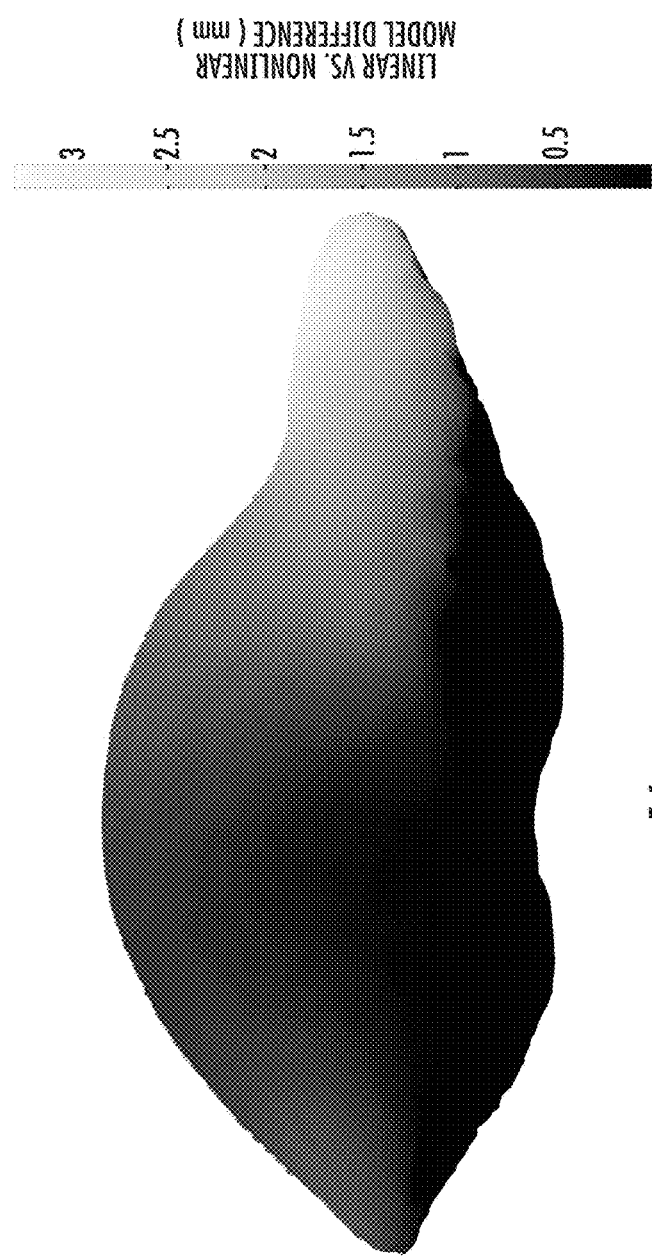
FIG. 16 shows the distribution of the euclidean difference between the two model displacement solutions.

Also tested was the assumption of linear elasticity by implementing a second model using a nonlinear, corotational finite element framework for comparison. Identical displacement boundary conditions on the support surfaces of both models were enforced, taken from the final registration solution for each of the five phantom cases referred to FIGS. 11A, 11B, 12A, and 12B. After solving both models for each case, the displacement fields from the two solutions were compared. Over this set of cases, the maximum euclidean distance between the location of any point in the linear model solution and the location of that same point in the nonlinear model solution was 3.3 mm, which occurred at the tip of the lobe in the FIG. 12B case. FIG. 16 shows the distribution of the euclidean difference between the two model displacement solutions for this case, with a linearization error of less than 1 mm for the vast majority of the volume. The other four cases exhibited similar patterns with even less linearization error.

One can consider this amount of linearization error to be relatively small when compared to the displacements exhibited in the phantom experiments (up to 23 mm, with element rotations as large as 30 degrees), suggesting that a linear model is perhaps adequate in this context. However, the importance of nonlinearities should not be minimized, as the linearization could potentially have much larger adverse effects depending on the nature and scale of the deformation. Care should always be taken to quantify, as done here, the expected amount of linearization error for the types of organ deformation being considered.

Currently, the computational trade-offs favor the linear approach for surgical guidance applications. In these phantom experiments, the total computation time for convergence of the proposed algorithm (8 iterations, 149 evaluations of the objective function) was approximately 13 seconds using a model with 8000 nodes and a surface point cloud containing approximately 4000 3D data points, using a MATLAB implementation on a standard laptop computer with a 2.67 GHz Intel Core i5 CPU. The total number of model solves required for the registration algorithm to converge is usually on the order of 100, so the increase in computation time required to implement a nonlinear model must be weighed against the potential loss of accuracy in linearization.

The linearization error should also be viewed in the context of the clinical data acquisition and registration problem, and compared to other potential sources of inaccuracy. Aside from the process of data acquisition itself, one source of potential registration inaccuracy comes from driving the registration problem with incomplete surface data having unknown or only approximate correspondence to the model surface. Another error source is the ability of the assumed boundary condition modes to actually reproduce the correct displacement field. It is estimated that these two sources combined contribute the majority of the target registration error.

As a case in point, once could have replaced the fast linear solve portion of the algorithm (which combined deformation modes via superposition as described above) with an iteratively solved corotational finite element framework. The nonrigid registration algorithm with the nonlinear model produced a mean TRE of 4.8 mm, compared to the mean TRE of 4.0 mm obtained with the linear model. When the subsurface tumor data was included, the nonlinear model produced a mean TRE of 3.4 mm, while the linear model produced a mean TRE of 3.3 mm. Thus, even though the nonlinear model represents the physical tissue mechanics more accurately than the linear model, random uncertainty and bias from other sources coincidentally caused the registration algorithm to perform slightly worse with the nonlinear model.

O. Clinical Feasibility Study

Figure 17A:
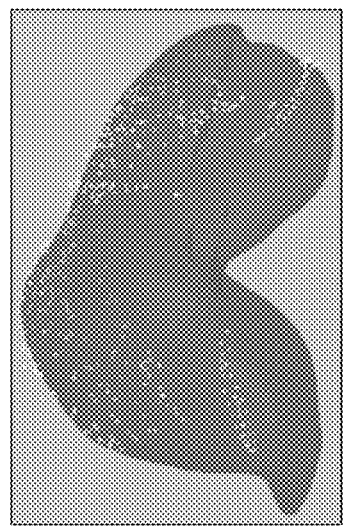
FIGS. 17A, 17B, 17C, and 17D show results from two clinical case studies with swab data from a tracked stylus.
Figure 17C:
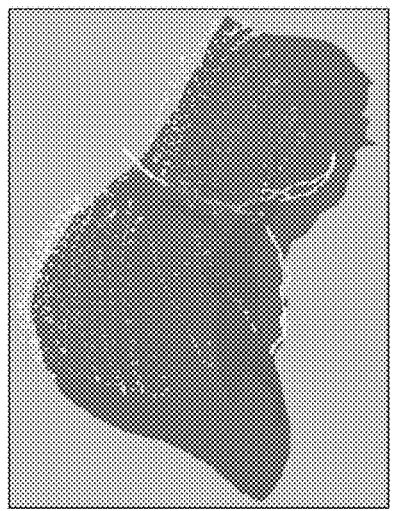
Figure 17B:
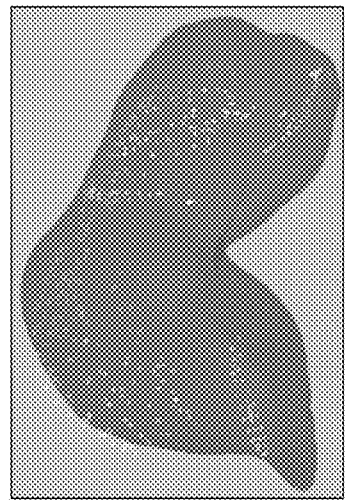
Figure 17D:
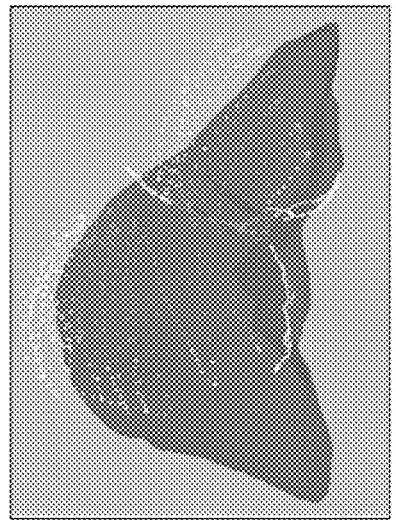

In addition to the phantom study, also investigated was the feasibility of the method in two clinical cases. Swabbed surface data collected with a tracked probe was used, which illustrates the versatility of the proposed method to handle sparse and noisy datasets. Since inaccuracies are introduced by intermittent stylus-to-tissue contact and local deformation due to stylus contact, the energy weighting coefficient was chosen as $\alpha_1 = 2 \times 10^{-4}$ to avoid fitting the data with unreasonably large deformations. The results of the nonrigid registration of the various embodiments are shown in FIGS. 17C and 17D, compared to the results in FIGS. 17A and 17B for a rigid registration using the method of [1]. Comparing FIGS. 17A and 17C, the average closest point normal distance between the model surface and the data improved from 4.5 mm for rigid registration to 2.4 mm for the nonrigid method. For FIGS. 17B and 17D, the closest point error improved from 7.4 mm for rigid registration to 3.0 mm This is significantly higher than the same surface metric for the representative phantom case (0.6 mm) owing to the different method of intraoperative data collection. Although acquiring exact point correspondences to evaluate TRE for clinical datasets is an ongoing research effort, one can infer that the mean surface TRE might show a similar relationship to the closest point surface metric as it shows in the representative phantom case where the closest point error was 0.6 mm and the mean TRE for targets on the surface was 3.3 mm.

P. Discussion

Figure 14A:
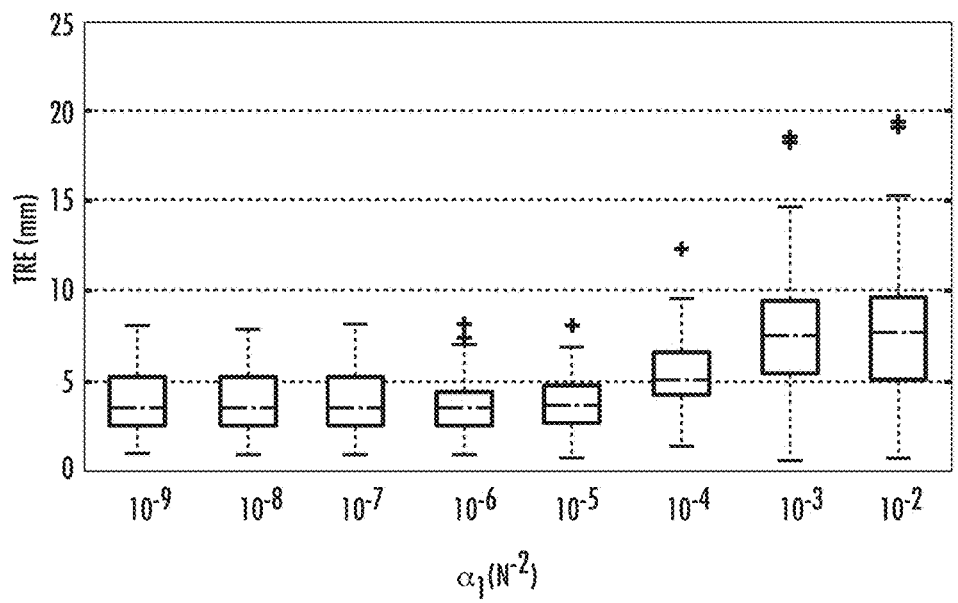
FIGS. 14A and 14B show statistical boxplots are shown illustrating the sensitivity of the results of the algorithm of the various embodiments to changes in the weighting coefficient 1 and the order n of the bivariate polynomial for the support surface displacements.
Figure 14B:
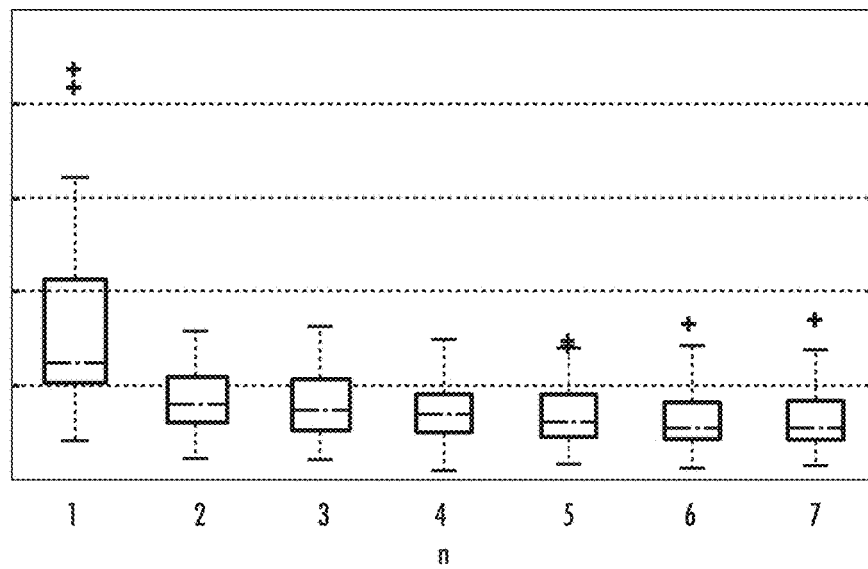

The distribution of TRE illustrated by the histograms in FIGS. 11B, 14A, and 14B show an average improvement in TRE from 9.5 mm to 3.3 mm over the five phantom experiments when the nonrigid registration approach is employed, and further improvement is shown when a single point of subsurface data was incorporated. In the analysis of the representative large-displacement phantom case with a dense distribution of fiducials, the proposed method demonstrate robustness to variations in initial registration, support surface designation, and the extent of available surface data. The effect of the energy weighting parameter and the number of support surface displacement modes was also investigated for this dataset, and a point of diminishing returns was shown. The comparison of linear and geometrically nonlinear tissue models demonstrates that linear models are capable of providing good guidance for this surgically realistic large-displacement case. Two cases using clinical data suggest that with an increased energy weighting, the method can provide a realistic deformation mapping driven by sparse noisy data acquired in the operating room.

With respect to accuracy needs in the clinical setting, previous studies have demonstrated that rigid organ-based registration errors are on the order of 1-2 cm routinely in clinical cases. Adding to this experience, the clinical conventional experience has considered the 1 cm negative margin to be the minimum acceptable resection threshold (as reported by a number of clinical studies). These would suggest that perhaps a surgeon's intuitive spatial understanding of the lesion between preoperative and intraoperative experience is compromised by organ deformation. In order to restore an intuitive spatial understanding to the surgeon, it would likely be beneficial to reduce target errors to below 5 mm on average (an accuracy threshold also suggested by others).

The results herein are the first to suggest that mean target registration errors less than 5 mm over the volume are possible using a sparse-surface-data driven mechanics-based nonrigid registration method. While other studies have suggested TREs less than 5 mm, the results were achieved with significantly more boundary condition information with very coarse TRE sampling in the former, and involved deformations significantly less than the clinical counterpart in the latter. In the various embodiments, the methods described herein need very little a priori boundary condition information and can be validated with a detailed spatial sampling of target error in experiments containing deformations that were carefully generated to mimic the clinical scenario.

It should also be noted that the methods described herein could also be feasible for laparoscopic procedures if enough surface data can be collected laparoscopically. The limitations on data collection in the laparoscopic case could be somewhat compensated for by the fact that the organ deformation is likely to be less extensive.

Figure 18:
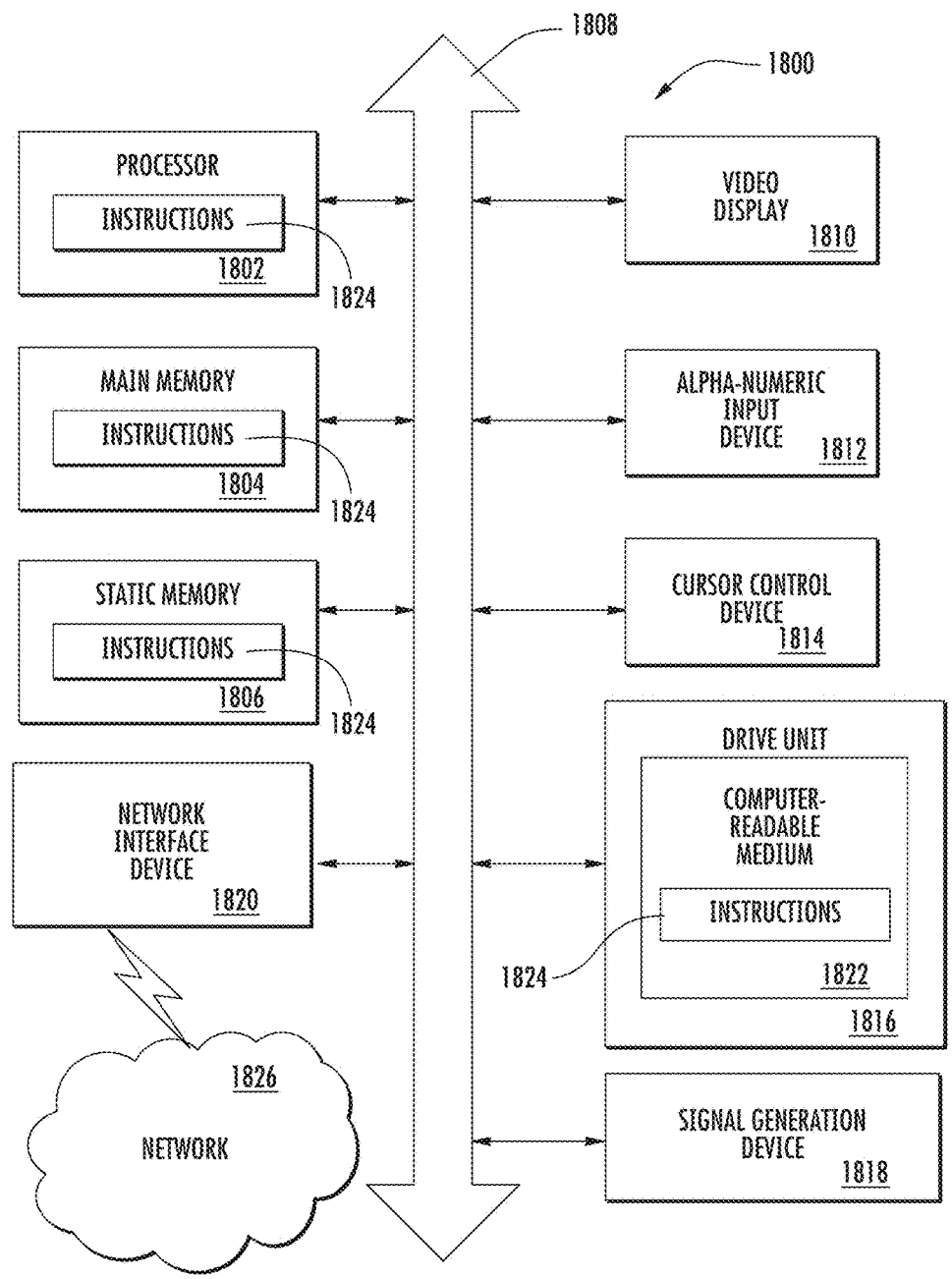
FIG. 18 is a schematic diagram of a computer system 1800 for executing a set of instructions that, when executed, can cause the computer system to perform one or more of the methodologies and procedures described herein.

FIG. 18 is a schematic diagram of a computer system 1800 for executing a set of instructions that, when executed, can cause the computer system to perform one or more of the methodologies and procedures described above. For example, the architecture of computer system 1800 can be used to describe the architecture of one or more components of FIG. 6. In some embodiments, the computer system 1800 operates as a standalone device. In other embodiments, the computer system 1800 can be connected (e.g., using a network) to other computing devices. In a networked deployment, the computer system 1800 can operate in the capacity of a server or a client developer machine in server-client developer network environment, or as a peer machine in a peer-to-peer (or distributed) network environment. In some embodiments, the system could be a plug-in card to the guidance system.

The machine can comprise various types of computing systems and devices, including a server computer, a client user computer, a personal computer (PC), a tablet PC, a laptop computer, a desktop computer, a control system, a network router, switch or bridge, or any other device capable of executing a set of instructions (sequential or otherwise) that specifies actions to be taken by that device. It is to be understood that a device of the present disclosure also includes any electronic device that provides voice, video or data communication. Further, while a single computer is illustrated, the phrase "computer system" shall be understood to include any collection of computing devices that individually or jointly execute a set (or multiple sets) of instructions to perform any one or more of the methodologies discussed herein.

The computer system 1800 can include a processor 1802 (such as a central processing unit (CPU), a graphics processing unit (GPU, or both), a main memory 1804 and a static memory 1806, which communicate with each other via a bus 1808. The computer system 1800 can further include a display unit 1810, such as a video display (e.g., a liquid crystal display or LCD), a flat panel, a solid state display, or a cathode ray tube (CRT)). The computer system 1800 can include an input device 1812 (e.g., a keyboard), a cursor control device 1814 (e.g., a mouse), a disk drive unit 1816, a signal generation device 1818 (e.g., a speaker or remote control) and a network interface device 1820.

The disk drive unit 1816 can include a computer-readable storage medium 1822 on which is stored one or more sets of instructions 1824 (e.g., software code) configured to implement one or more of the methodologies, procedures, or functions described herein. The instructions 1824 can also reside, completely or at least partially, within the main memory 1804, the static memory 1806, and/or within the processor 1802 during execution thereof by the computer system 1800. The main memory 1804 and the processor 1802 also can constitute machine-readable media.

Dedicated hardware implementations including, but not limited to, application-specific integrated circuits, programmable logic arrays, and other hardware devices can likewise be constructed to implement the methods described herein. Applications that can include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the exemplary system is applicable to software, firmware, and hardware implementations.

In accordance with various embodiments of the present disclosure, the methods described herein can be stored as software programs in a computer-readable storage medium and can be configured for running on a computer processor. Furthermore, software implementations can include, but are not limited to, distributed processing, component/object distributed processing, parallel processing, virtual machine processing, which can also be constructed to implement the methods described herein.

The present disclosure contemplates a computer-readable storage medium containing instructions 1824 or that receives and executes instructions 1824 from a propagated signal so that a device connected to a network environment 1826 can send or receive voice and/or video data, and that can communicate over the network 1826 using the instructions 1824. The instructions 1824 can further be transmitted or received over a network 1826 via the network interface device 1820.

While the computer-readable storage medium 1822 is shown in an exemplary embodiment to be a single storage medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any device that is capable of storing a set of instructions for execution by the machine and that cause the machine to perform any one or more of the methodologies of the present disclosure.

The term "computer-readable medium" shall accordingly be taken to include, but not be limited to, solid-state memories such as a memory card or other package that houses one or more read-only (non-volatile) memories, random access memories, or other re-writable (volatile) memories; magneto-optical or optical medium such as a disk or tape; as well as carrier wave signals such as a signal embodying computer instructions in a transmission medium; and/or a digital file attachment to e-mail or other self-contained information archive or set of archives considered to be a distribution medium equivalent to a tangible storage medium. Accordingly, the disclosure is considered to include any one or more of a computer-readable medium or a distribution medium, as listed herein and to include recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same functions are considered equivalents.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

REFERENCES

The following documents are referred to through the instant application and their contents are hereby incorporated by reference in their entirety:

[1] L. W. Clements, W. C. Chapman, B. M. Dawant, R. L. Galloway, and M. I. Miga, "Robust surface registration using salient anatomical features for image-guided liver surgery: Algorithm and validation," Medical Physics, vol. 35, no. 6, pp. 2528-2540, 2008.

[2] B. Dawant, S. Pan, and R. Li, "Robust segmentation of medical images using geometric deformable models and a dynamic speed function," Proc. Med. Image Comput. Comput.-Assist. Intervent. (MICCAI 2001) (Lecture Notes in Computer Science, vol. 2208), pp. 1040-1047.

[3] S. Pan and B. M. Dawant, "Automatic 3d segmentation of the liver from abdominal ct images: A level-set approach," Medical Imaging 2001: Image Processing, Proc. SPIE, vol. 4322, M. Sonka and K. Hanson, Eds., p. 128138.

[4] J. A. Sethian, "Level set methods and fast marching methods: Evolving interfaces in computational geometry, fluid mechanics, computer vision, and materials science," Cambridge, U.K.: Cambridge Univ. Press, 1999.

What is claimed is:

1. A method for collecting and processing physical space data for use while performing an image-guided surgical (IGS) procedure, the method comprising:
    performing a first rigid alignment of a preoperative, three-dimensional, biomechanical computer model of a non-rigid structure of interest in a patient and surface data in a patient space associated with a portion of said non-rigid structure during an intraoperative presentation of the non-rigid structure,
    wherein the surface data comprises both anterior surface data of the non-rigid structure of interest and posterior surface data of the non-rigid structure of interest;
    defining a set of deformation modes for the computer model based on a configuration of an intraoperative supporting surface of the non-rigid structure during the intraoperative presentation; and
    computing a deformation of the computer model that provides a non-rigid alignment of said computer model and the surface data, the computing comprising:
    selecting a set of basis functions and a degree for the set of basis functions that parameterize the set of deformation modes and
    selecting a corresponding set of parameters for the parameterized set of deformation modes,
    obtaining a deformed version of the computer model based on the selected set of parameters and selected the set of basis functions,
    evaluating whether the deformed version of the computer model fits the surface data,
    wherein the evaluating includes determining whether a posterior side of the deformed version of the computer model fits the anterior surface data; and
    repeating the obtaining and the evaluating with an updated set of parameters for the selected set of basis functions until the deformed version of the computer model fits the surface data.

2. The method of claim 1, wherein a functional form of the selected set of basis functions comprises at least one among a continuous functional form, an overlapping functional form, or multi-domain coupled functional form.

3. The method of claim 1, further comprising incorporating contributing deformations from parameters being varied in the updated set of parameters.

4. The method of claim 1, wherein the obtaining comprises:

calculating first displacements for a portion of the computer model corresponding to the surface data based on the selected set of parameters and the selected set of basis functions,
calculating second displacements for other portions of the computer model while enforcing the first displacements, and
applying the first displacements and the second displacements to the computer model to yield the deformed version of the computer model.

5. The method of claim 1, wherein the evaluating comprises:
performing a second rigid alignment of the surface data and the deformed version of the computer model;
calculating a closeness metric between the surface data and the deformed version of the computer model after the second rigid alignment, and
determining that the deformed version of the computer model fits the surface data when at least the closeness metric meets a termination criteria.

6. The method of claim 5, wherein the determining further comprises:
determining that the deformed version of the computer model fits the surface data when a history of the closeness metric meets a termination criteria.

7. A computer-readable storage medium, having stored thereon a computer program for causing a computing device to perform a method for collecting and processing physical space data for use while performing an image-guided surgical (IGS) procedure, the computer program comprising a plurality of code sections for:
performing a first rigid alignment of a preoperative, three-dimensional, biomechanical computer model of a non-rigid structure of interest in a patient and surface data in a patient space associated with a portion of said non-rigid structure during an intraoperative presentation of the non-rigid structure,
wherein the surface data comprises both anterior surface data of the non-rigid structure of interest and posterior surface data of the non-rigid structure of interest;
defining a set of deformation modes for the computer model based on the intraoperative presentation; and
computing a deformation of the computer model that provides a non-rigid alignment of said computer model and the surface data, the computing comprising:
selecting a set of basis functions and a degree for the set of basis functions that parameterize the set of deformation modes and a corresponding set of parameters for the parameterized set of deformation modes,
obtaining a deformed version of the computer model based on the selected set of parameters and the selected set of basis functions,
evaluating whether the deformed version of the computer model fits the surface data,
wherein the evaluating includes determining whether a posterior side of the deformed version of the computer model fits the anterior surface data; and
repeating the obtaining and the evaluating with an updated set of parameters for the selected set of basis functions until the deformed version of the computer model fits the surface data.

8. The computer-readable medium of claim 7, wherein a functional form of the selected set of basis functions comprises at least one among a continuous functional form, an overlapping functional form, or multi-domain coupled functional form.

9. The computer-readable medium of claim 7, the computer program comprising a plurality of code sections for incorporating contributing deformations from parameters being varied in the updated set of parameters.

10. The computer-readable storage medium of claim 7, wherein the obtaining comprises:
calculating first displacements for a portion of the computer model corresponding to the surface data based on the selected set of parameters and the selected set of basis functions,
calculating second displacements for other portions of the computer model while enforcing the first displacements, and
applying the first displacements and the second displacements to the computer model to yield the deformed version of the computer model.

11. The computer-readable storage medium of claim 7, wherein the evaluating comprises:
performing a second rigid alignment of the surface data and the deformed version of the computer model;
calculating a closeness metric between the surface data and the deformed version of the computer model after the second rigid alignment, and
determining that the deformed version of the computer model fits the surface data when at least the closeness metric meets a termination criteria.

12. The computer-readable storage medium of claim 11, wherein the determining further comprises:
determining that the deformed version of the computer model fits the surface data when a history of the closeness metric meets a termination criteria.

* * * * *